(12) United States Patent
Sasaki

(10) Patent No.: US 8,723,937 B2
(45) Date of Patent: May 13, 2014

(54) ENDOSCOPE SYSTEM, IMAGING APPARATUS, AND CONTROL METHOD

(75) Inventor: Hiroshi Sasaki, Hachioji (JP)

(73) Assignee: Olympus Corporation, Tokyo (JP)

( * ) Notice: Subject to any disclaimer, the term of this patent is extended or adjusted under 35 U.S.C. 154(b) by 441 days.

(21) Appl. No.: 13/049,055

(22) Filed: Mar. 16, 2011

(65) Prior Publication Data

US 2011/0228064 A1 Sep. 22, 2011

(30) Foreign Application Priority Data

Mar. 18, 2010 (JP) .................................. 2010-062887

(51) Int. Cl.
*H04N 7/18* (2006.01)
*A62B 1/04* (2006.01)

(52) U.S. Cl.
USPC .............................................. 348/65; 348/61

(58) Field of Classification Search
None
See application file for complete search history.

(56) References Cited

U.S. PATENT DOCUMENTS

| 5,764,292 A * | 6/1998 | Yamaguchi | 348/363 |
| 2007/0055104 A1* | 3/2007 | Kumei et al. | 600/176 |
| 2007/0167867 A1* | 7/2007 | Wolf | 600/561 |
| 2010/0097454 A1* | 4/2010 | Kubo et al. | 348/65 |

FOREIGN PATENT DOCUMENTS

| JP | 8-37604 A | 2/1996 |
| JP | 08-181909 | 7/1996 |
| JP | 10-225427 | 8/1998 |
| JP | 2003-134393 A | 5/2003 |
| JP | 2007-50110 A | 3/2007 |
| JP | 2009-219719 A | 10/2009 |

OTHER PUBLICATIONS

Japanese Office Action dated Apr. 23, 2013 from corresponding Japanese Patent Application No. JP 2010-062887, together with an English language translation.

* cited by examiner

*Primary Examiner* — Chikaodili E Anyikire
(74) *Attorney, Agent, or Firm* — Scully, Scott, Murphy & Presser, P.C.

(57) ABSTRACT

An endoscope system includes an imaging section that includes an optical system and an imaging element, an observation mode setting section that sets an object observation mode, a diaphragm control section that selects a diaphragm state based on the observation mode, and an image processing section that processes an image acquired by the imaging section. The diaphragm control section selecting a first diaphragm state when the observation mode is a first observation mode. The first diaphragm state being a state in which a resolution determined by a diffraction limit based on a diaphragm of the optical system is lower than a resolution determined by the imaging element. The diaphragm control section selecting a second diaphragm state when the observation mode is a second observation mode. The second diaphragm state being a state in which the resolution determined by the diffraction limit based on the diaphragm of the optical system is equal to or higher than the resolution determined by the imaging element.

19 Claims, 21 Drawing Sheets

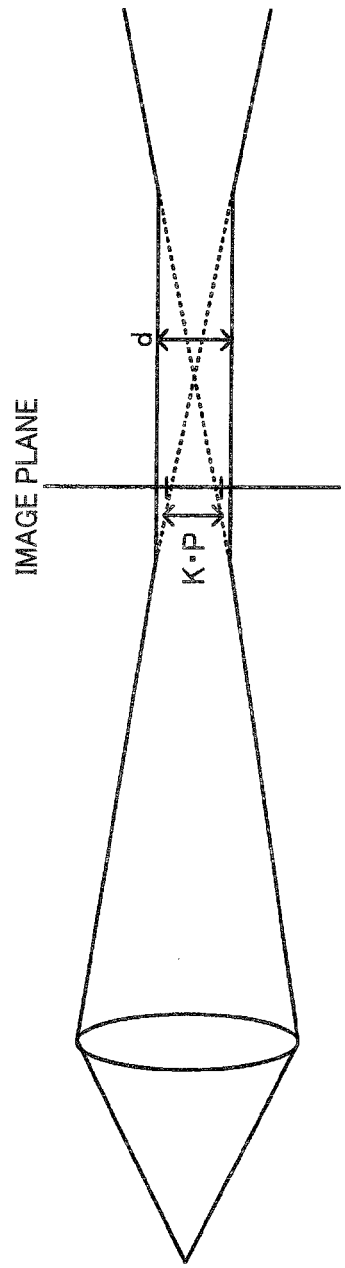

DISTANT OBSERVATION

CLOSE OBSERVATION

ENDOSCOPE SYSTEM, IMAGING APPARATUS, AND CONTROL METHOD

Japanese Patent Application No. 2010-062887 filed on Mar. 18, 2010, is hereby incorporated by reference in its entirety.

BACKGROUND

The present invention relates to an endoscope system, an imaging apparatus, a control method, and the like.

An imaging apparatus such as an endoscope may be required to generate a deep-focus image inside a body cavity in order to facilitate a doctor's diagnosis. This has been achieved by increasing the depth of field of an endoscope by utilizing an optical system having a relatively large diaphragm value (hereinafter may be referred to as "F-number").

In recent years, an imaging element having about several hundred thousand pixels has been used for endoscope systems. The depth of field of an optical system is determined by the size of the permissible circle of confusion. Since an imaging element having a large number of pixels has a small pixel pitch and a small permissible circle of confusion, the depth of field of the imaging apparatus decreases. In this case, the depth of field may be maintained by increasing the diaphragm value of the optical system. According to this method, however, the optical system darkens, and noise increases. Therefore, the image quality deteriorates. Moreover, the effects of diffraction increase as the diaphragm value increases, so that the imaging performance deteriorates. Accordingly, a high-resolution image cannot be obtained even if the number of pixels of the imaging element is increased.

JP-A-10-225427 aims at obtaining a practical depth of field by increasing the size of the permissible circle of confusion along with a change in diaphragm value, and changing the reading pixel size of the imaging element to be almost equal to the size of the permissible circle of confusion. A sufficient depth of field is thus obtained while ensuring a sufficient quantity of light when imaging a dark object.

JP-A-8-181909 discloses suppressing a change in resolution based on the diaphragm value. In JP-A-8-181909, a constant resolution is obtained independently of the diaphragm value by decreasing the degree of contour enhancement when decreasing the diaphragm value of the optical system, and increasing the degree of contour enhancement when increasing the diaphragm value of the optical system.

SUMMARY

According to one aspect of the invention, there is provided an endoscope system comprising:
an imaging section that includes an optical system and an imaging element;
an observation mode setting section that sets an object observation mode;
a diaphragm control section that selects a diaphragm state based on the observation mode set by the observation mode setting section; and
an image processing section that processes an image acquired by the imaging section,
the diaphragm control section selecting a first diaphragm state when the observation mode is a first observation mode, the first diaphragm state being a state in which a resolution determined by a diffraction limit based on a diaphragm of the optical system is lower than a resolution determined by the imaging element, and
the diaphragm control section selecting a second diaphragm state when the observation mode is a second observation mode, the second diaphragm state being a state in which the resolution determined by the diffraction limit based on the diaphragm of the optical system is equal to or higher than the resolution determined by the imaging element.

According to another aspect of the invention, there is provided a control method comprising:
setting an object observation mode;
selecting a first diaphragm state when the observation mode is a first observation mode, the first diaphragm state being a state in which a resolution determined by a diffraction limit based on a diaphragm of an optical system is lower than a resolution determined by an imaging element; and
selecting a second diaphragm state when the observation mode is a second observation mode, the second diaphragm state being a state in which the resolution determined by the diffraction limit based on the diaphragm of the optical system is equal to or higher than the resolution determined by the imaging element.

According to another aspect of the invention, there is provided an imaging apparatus comprising:
an imaging section that includes an optical system and an imaging element;
an observation mode setting section that sets an object observation mode; and
a diaphragm control section that selects a diaphragm value based on the observation mode set by the observation mode setting section,
the diaphragm control section selecting a first diaphragm state as the diaphragm value when the observation mode is a first observation mode, the first diaphragm state being a state in which a resolution determined by a diffraction limit based on a diaphragm of the optical system is lower than a resolution determined by the imaging element, and
the diaphragm control section selecting a second diaphragm state as the diaphragm value when the observation mode is a second observation mode, the second diaphragm state being a state in which the resolution determined by the diffraction limit based on the diaphragm of the optical system is equal to or higher than the resolution determined by the imaging element.

BRIEF DESCRIPTION OF THE DRAWINGS

FIG. 6 shows an example when the Airy disk diameter d is larger than the size K·P of the permissible circle of confusion.

DESCRIPTION OF EXEMPLARY EMBODIMENTS

Figure 1A:
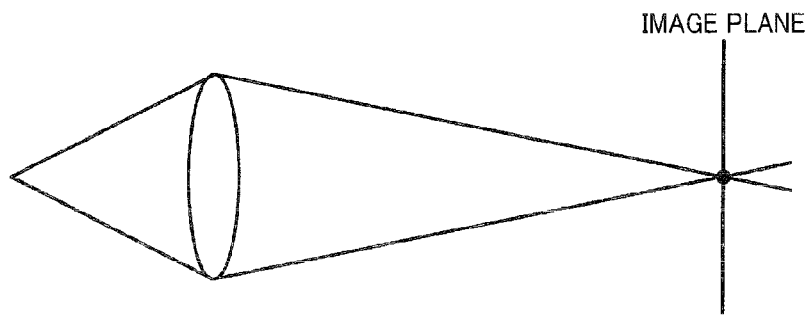
FIG. 1A shows an example of convergence of light without taking account of the diffraction limit.

Several aspects of the invention may provide an endoscope system, a control method, an imaging apparatus, and the like that can acquire an image at the original resolution of an imaging element, and can increase the depth of field taking account of the effects of the diffraction limit.

Several aspects of the invention may provide an endoscope system, a control method, an imaging apparatus, and the like that can acquire an image at the original resolution of an imaging element, and can reduce noise using a variable diaphragm, even when using an imaging element having a pixel pitch that does not allow the circle of confusion to be included within the permissible circle of confusion due to the effects of the diffraction limit as a result of increasing the F-number in order to obtain a practical depth of field.

According to one embodiment of the invention, there is provided an endoscope system comprising:

an imaging section that includes an optical system and an imaging element;

an observation mode setting section that sets an object observation mode;

a diaphragm control section that selects a diaphragm state based on the observation mode set by the observation mode setting section; and an image processing section that processes an image acquired by the imaging section, the diaphragm control section selecting a first diaphragm state when the observation mode is a first observation mode, the first diaphragm state being a state in which a resolution determined by a diffraction limit based on a diaphragm of the optical system is lower than a resolution determined by the imaging element, and the diaphragm control section selecting a second diaphragm state when the observation mode is a second observation mode, the second diaphragm state being a state in which the resolution determined by the diffraction limit based on the diaphragm of the optical system is equal to or higher than the resolution determined by the imaging element.

According to the above embodiment, the observation mode is set. The first diaphragm state is selected in the first observation mode, and the second diaphragm state is selected in the second observation mode. In the first diaphragm state, the resolution determined by the diffraction limit based on the diaphragm of the optical system is lower than the resolution determined by the imaging element. In the second diaphragm state, the resolution determined by the diffraction limit based on the diaphragm of the optical system is equal to or higher than the resolution determined by the imaging element.

Therefore, the diaphragm state can be appropriately determined depending on the observation mode, and it is possible to set a diaphragm state in which the resolution decreases due to the effects of the diffraction limit, and a diaphragm state in which a high resolution can be maintained by suppressing the effects of the diffraction limit.

According to another embodiment of the invention, there is provided a control method comprising:

setting an object observation mode;

selecting a first diaphragm state when the observation mode is a first observation mode, the first diaphragm state being a state in which a resolution determined by a diffraction limit based on a diaphragm of an optical system is lower than a resolution determined by an imaging element; and selecting a second diaphragm state when the observation mode is a second observation mode, the second diaphragm state being a state in which the resolution determined by the diffraction limit based on the diaphragm of the optical system is equal to or higher than the resolution determined by the imaging element.

According to the above embodiment, it is possible to implement a control method that can appropriately determine the diaphragm state depending on the observation mode, and can set a diaphragm state in which the resolution decreases due to the effects of the diffraction limit, and a diaphragm state in which a high resolution can be maintained by suppressing the effects of the diffraction limit.

According to another embodiment of the invention, there is provided an imaging apparatus comprising:

an imaging section that includes an optical system and an imaging element;

an observation mode setting section that sets an object observation mode; and a diaphragm control section that selects a diaphragm value based on the observation mode set by the observation mode setting section, the diaphragm control section selecting a first diaphragm state as the diaphragm value when the observation mode is a first observation mode, the first diaphragm state being a state in which a resolution determined by a diffraction limit based on a diaphragm of the optical system is lower than a resolution determined by the imaging element, and the diaphragm control section selecting a second diaphragm state as the diaphragm value when the observation mode is a second observation mode, the second diaphragm state being a state in which the resolution determined by the diffraction limit based on the diaphragm of the optical system is equal to or higher than the resolution determined by the imaging element.

According to the above embodiment, it is possible to implement an imaging apparatus that can appropriately determine the diaphragm state depending on the observation mode, and can set a diaphragm state in which the resolution decreases due to the effects of the diffraction limit, and a diaphragm state in which a high resolution can be maintained by suppressing the effects of the diffraction limit.

Exemplary embodiments of the invention are described below. Note that the following embodiments do not in any way limit the scope of the invention laid out in the claims. Note also that all elements of the following embodiments should not necessarily be taken as essential requirements for the invention.

1. Method

Figure 1B:
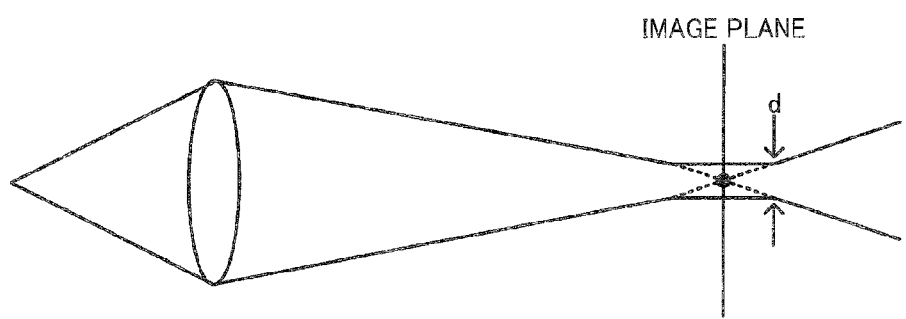
FIG. 1B shows an example of convergence of light taking account of the diffraction limit.

The meanings of the terms "diffraction limit" and "Airy disk" are described below. Since light has wave properties, a diffraction phenomenon occurs. Therefore, light is not converged (focused) at an infinitely small point (see FIG. 1A), but has a certain size at the convergence point (see FIG. 1B). This limit is referred to as "diffraction limit", and a spot formed by converged light is referred to as "Airy disk". In FIG. 1B, d indicates the Airy disk diameter.

Figure 2:
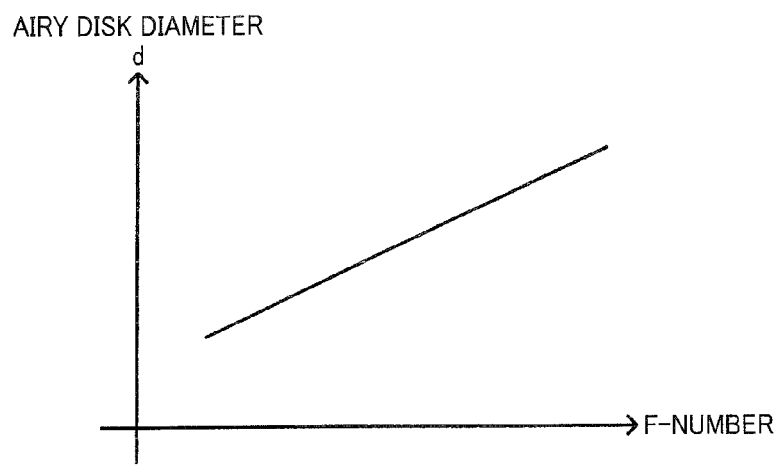
FIG. 2 is a view showing the relationship between the Airy disk diameter d and the F-number F.

The Airy disk diameter d increases when increasing the F-number (i.e., stopping down the diaphragm). The Airy disk diameter d and the F-number have a relationship shown in FIG. 2.

Figure 3:
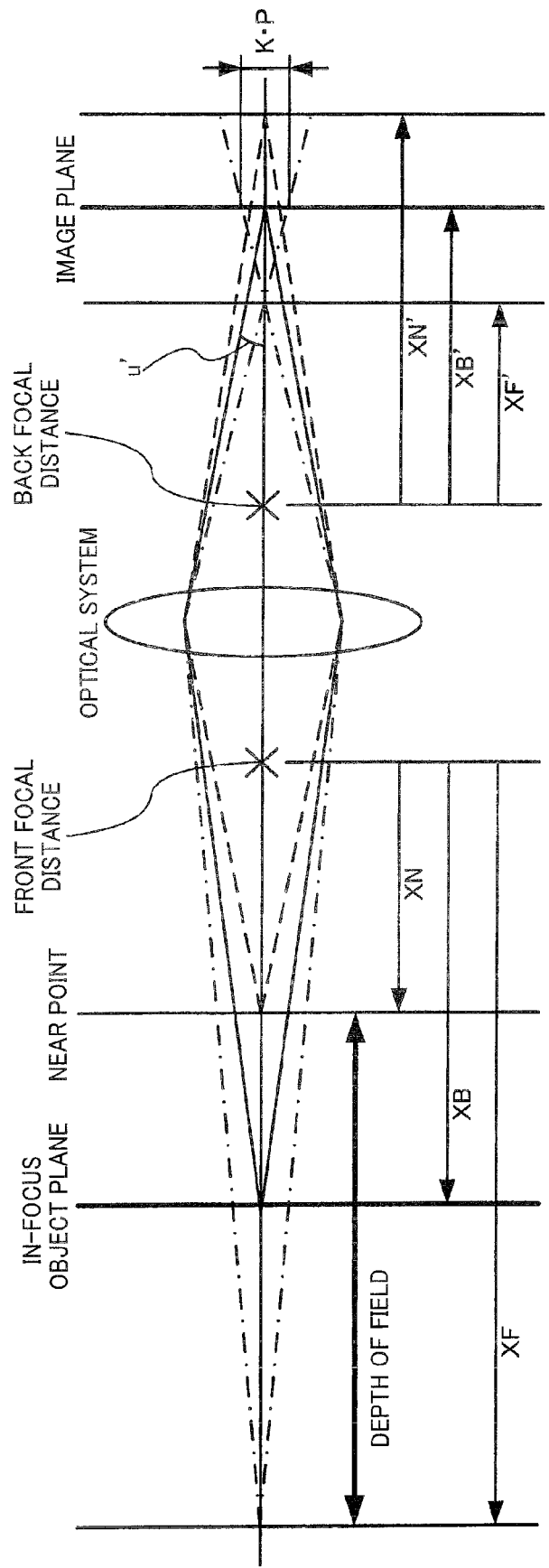
FIG. 3 is a view illustrative of the depth of field.

The depth of field is described in detail below with reference to FIG. 3. In FIG. 3, a right arrow indicates a vector having a positive value, and a left arrow indicates a vector having a negative value. When an imaging element having a pixel pitch (vertical and horizontal dimensions of one pixel) of P is disposed at a distance XB' from the back focal distance of the optical system, the position of the object (in-focus object plane) where the optical system has the best imaging performance in the image plane of the imaging element is the position at a distance XB from the front focal distance of the optical system. The distance XB is uniquely calculated by the following Newton's equation using the distance XB'. Note that f is the focal length of the optical system.

$$XB \cdot XB' = -f^2 \quad (1)$$

When the object is moved to the position at a distance XN from the front focal distance of the optical system, the image plane position XN' moves from the image plane in the direction opposite to the optical system. However, when the diameter of the circle of confusion in the image plane is smaller than the resolution K·P (where, K is a coefficient determined by a filter array and an interpolation process) of the imaging apparatus, the object positioned at the distance XN from the front focal distance of the optical system is considered to be in focus. In this case, the resolution K·P is determined to be the diameter of the permissible circle of confusion.

A range in which the diameter of the circle of confusion in the image plane is equal to or smaller than the resolution K·P is defined as the near point-side depth of field, and the position of the object where the diameter of the circle of confusion coincides with the resolution K·P is hereinafter referred to as "near point". The position of the near point is hereinafter expressed by the position at the distance XN from the front focal distance. The above definition is similarly applied to the far point-side depth of field. The far point-side position of the object where the diameter of the circle of confusion coincides with the resolution K·P is hereinafter referred to as "far point". The position of the far point is hereinafter expressed by the position at the distance XF from the front focal distance.

The diameter of the circle of confusion in the image plane when the object is positioned at the near point is approximated by $2(XN'-XB') \cdot NA'$ using the numerical aperture NA ($=\sin(u')$) (where, u' is the angle formed by the optical axis and a beam that enters the image plane shown in FIG. 3) of the optical system.

Since the diameter of the circle of confusion coincides with the resolution K·P when the object is positioned at the near point, the following expression (2) is obtained.

$$2(XN'-XB') \cdot NA' = K \cdot P \quad (2)$$

Transforming the expression (2) using the following expression (3) (i.e., a relational expression of the F-number and the numerical aperture) yields the following expression (4). Note that F is the F-number of the optical system.

$$F = \frac{1}{2NA'} \quad (3)$$

$$XN' - XB' = K \cdot P \cdot F \quad (4)$$

Transforming the expression (4) using Newton's equation (1) yields the following expression (5) (i.e., a relational expression of the near point-side depth of field).

$$\frac{1}{XB} - \frac{1}{XN} = \frac{K \cdot P \cdot F}{f^2} \quad (5)$$

A relational expression of the far point-side depth of field calculated in the same manner as the near point-side depth of field is shown by the following expression (6).

$$\frac{1}{XF} - \frac{1}{XB} = \frac{K \cdot P \cdot F}{f^2} \quad (6)$$

The expressions (5) and (6) can be transformed into the following expressions. The near point (i.e., the position at the distance XN from the front focal distance) and the far point (i.e., the position at the distance XF from the front focal distance) can be calculated using the following expressions.

$$XN = \frac{f^2 \cdot XB}{f^2 - KPF \cdot XB} \quad (7)$$

$$XF = \frac{f^2 \cdot XB}{f^2 + KPF \cdot XB} \quad (8)$$

Specifically, when the focal length f, the F-number F, the coefficient K, and the in-focus object plane distance XB of the optical system are constant, the near point and the far point approach the in-focus object plane (i.e., the depth of field decreases) as the resolution K·P of the imaging apparatus decreases.

The depth of field can be increased by increasing the F-number F or the coefficient K of the resolution K·P of the imaging apparatus. The following description illustrates an example in which the coefficient K is constant, and the depth of field is changed by changing the F-number F.

Figure 4:
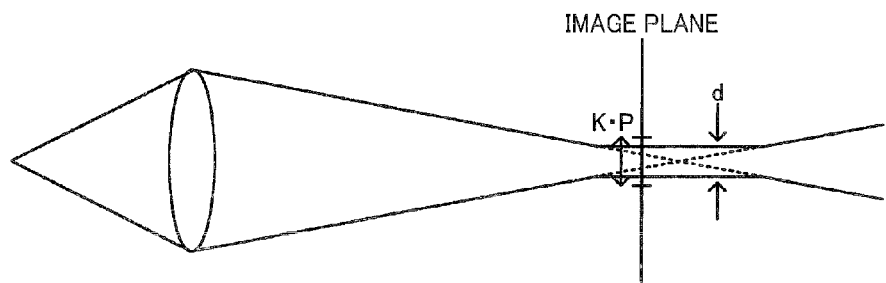
FIG. 4 shows an example when the Airy disk diameter d is smaller than the size K·P of the permissible circle of confusion.
Figure 5A:
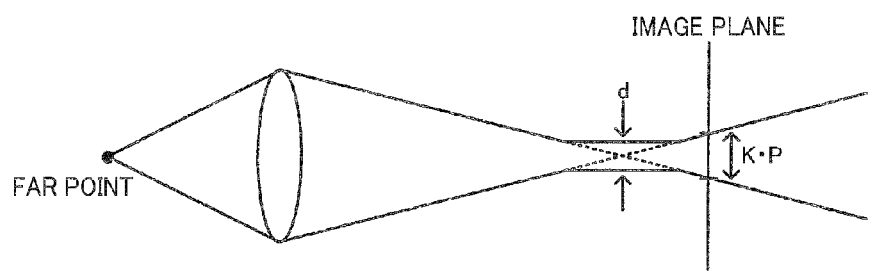
FIG. 5A is a view illustrative of the far point of the depth of field.
Figure 5B:
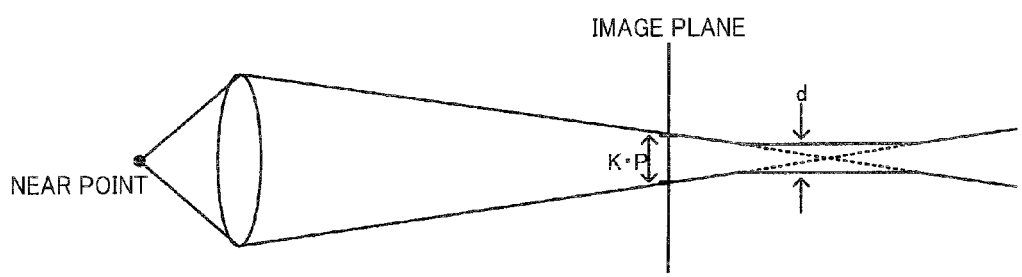
FIG. 5B is a view illustrative of the near point of the depth of field.

The relationship between the permissible circle of confusion and the Airy disk is described below. When the Airy disk diameter d is smaller than the size (K·P) of the permissible circle of confusion (see FIG. 4), the depth of field is determined by the above concept (see FIGS. 5A and 5B).

When the Airy disk diameter d is larger than the size (K·P) of the permissible circle of confusion (see FIG. 6), the depth of field is determined by the Airy disk diameter d instead of the size (K·P) of the permissible circle of confusion. As shown in FIG. 6, since the size of the circle of confusion is equal to or larger than the Airy disk diameter d, the size of the circle of confusion does not become equal to or smaller than the Airy disk diameter d even when the object is in focus. In this case, the size of the permissible circle of confusion is the Airy disk diameter d.

Figure 7A:
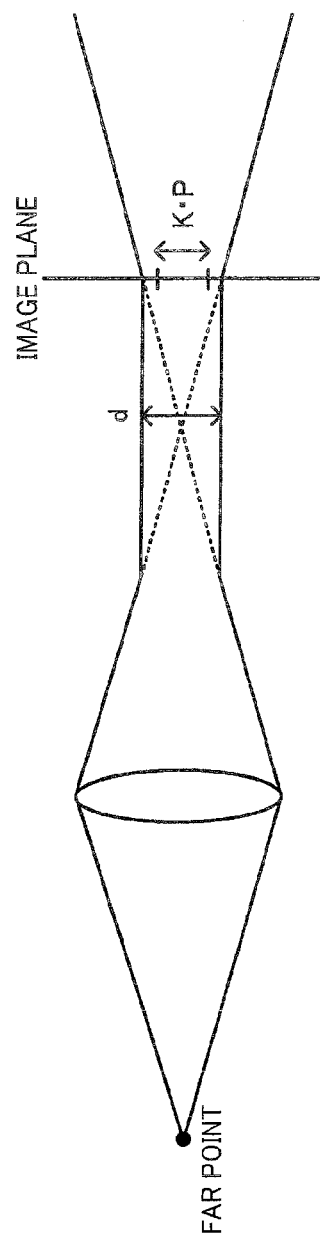
FIG. 7A is a view illustrative of the far point of the depth of field.
Figure 7B:
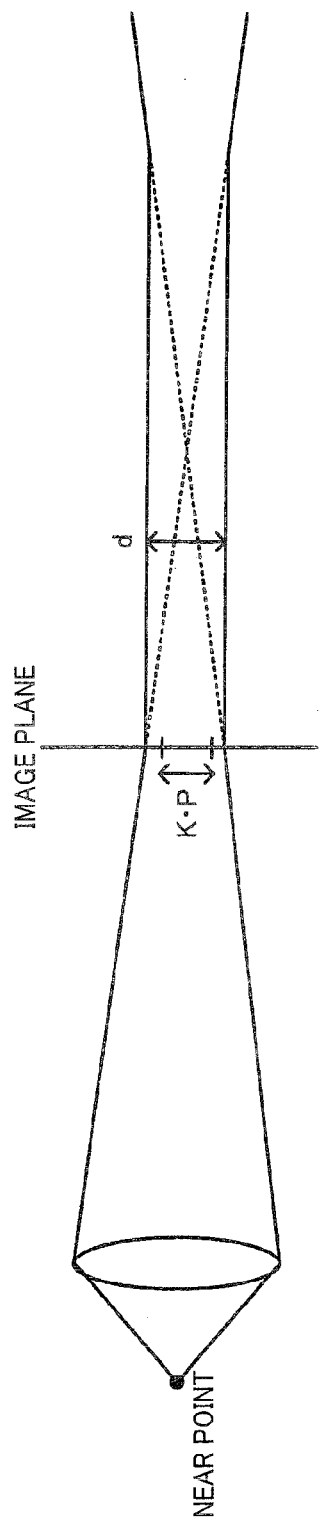
FIG. 7B is a view illustrative of the near point of the depth of field.

Therefore, the depth of field can be increased (see FIGS. 7A and 7B) although the resolution decreases due to an increase in the size of the permissible circle of confusion.

A method that sets a first observation mode in which d>K·P and a second observation mode in which d<K·P, and implements deep focus (i.e., a state in which the depth of field is deep) while acquiring an image at a resolution that utilizes the performance of the imaging apparatus to a maximum extent by utilizing the first observation mode and the second observation mode, has been proposed.

In the first observation mode, the depth of field is increased in spite of a decrease in resolution by increasing the F-number (stopping down the diaphragm) (i.e., increasing the effects of the diffraction limit). In the second observation mode, an image at a high resolution determined by the imaging apparatus is acquired in spite of a shallow depth of field by decreasing the F-number (i.e., suppressing the effects of the diffraction limit).

Figure 8:
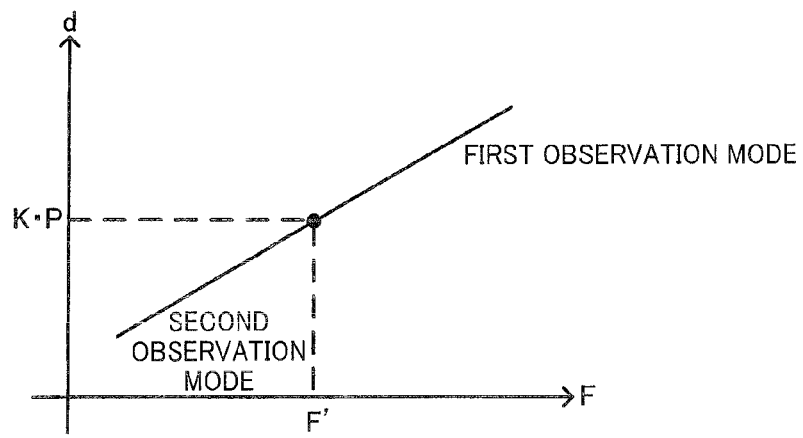
FIG. 8 is a view showing the relationship between a first observation mode and a second observation mode.

FIG. 8 is illustrative of the first observation mode and the second observation mode. For example, the observation mode is determined to be the first observation mode or the second observation mode based on the point where d=K·P.

An advantage obtained by utilizing the first observation mode when implementing deep focus is described below.

Figure 9:
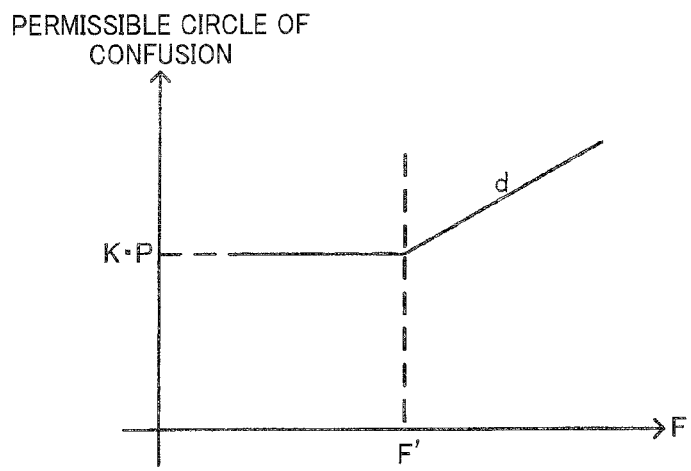
FIG. 9 is a view showing the relationship between the F-number F and the size of the permissible circle of confusion.

When the F-number at the boundary between the first observation mode and the second observation mode is referred to as F', the F-number and the permissible circle of confusion have a relationship shown in FIG. 9. When the F-number is smaller than F', the size of the permissible circle of confusion is constant at K·P. When the F-number is larger than F', the size of the permissible circle of confusion is determined by the Airy disk diameter d. Since the Airy disk diameter d increases as the F-number increases (see FIG. 8), the size of the permissible circle of confusion increases in the first observation mode as the F-number increases (see FIG. 9).

Figure 10:
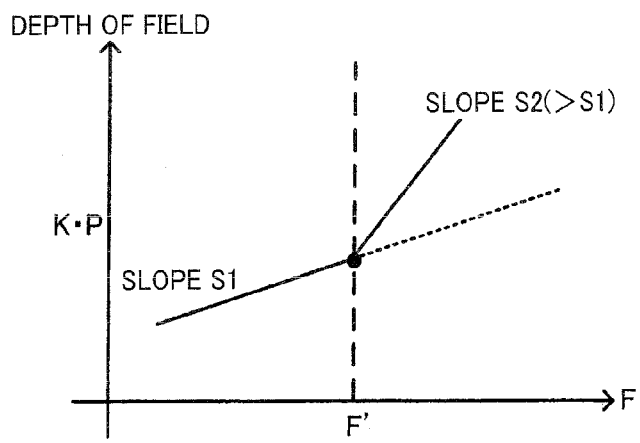
FIG. 10 is a view showing the relationship between the F-number F and the depth of field.

The depth of field increases as the F-number increases, and also increases as the size of the permissible circle of confusion increases, as described above. Specifically, the depth of field and the F-number have a relationship shown in FIG. 10. When the F-number is smaller than F' (second observation mode), the depth of field increases along a slope S1 as the F-number increases. When the F-number is larger than F' (first observation mode), the depth of field increases along a slope S2 (S2>S1) due to an increase in the F-number and an increase in the size of the permissible circle of confusion.

Figure 11:
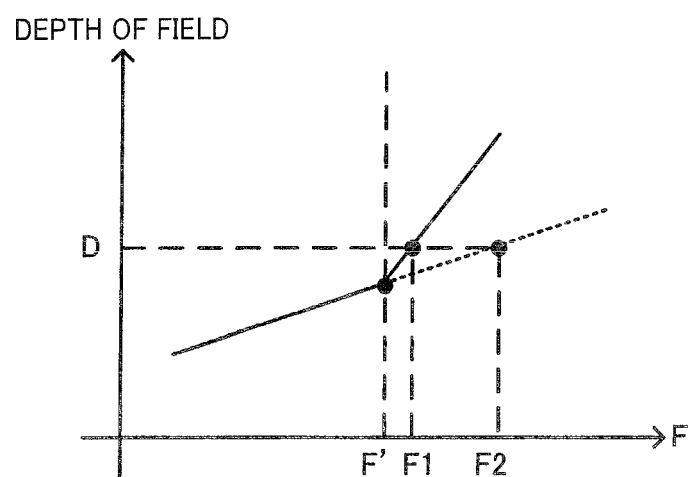
FIG. 11 is a view illustrative of the F-number F that implements the depth of field D.

Therefore, the increase rate of the depth of field due to an increase in the F-number can be increased as compared with the case of using the mode (second observation mode) in which the effects in the diffraction limit are suppressed. This makes it possible to implement the desired depth of field using a small F-number as compared with the case of using the second observation mode. FIG. 11 is illustrative of the above advantage. When using the second observation mode, it is necessary to set the F-number to F2 in order to implement the desired depth of field D. When using the first observation mode, however, the desired depth of field D can be implemented by setting the F-number to F1 (F1<F2).

Specifically, since a small F-number can be used when implementing the depth of field D, a brighter image can be obtained. This is particularly effective for a system that tends to generate a dark image due to a small quantity of light (e.g., narrow-band observation (e.g., NBI) employed for an endoscope system).

An endoscope system according to one embodiment of the invention that implements the above method includes an imaging section, an observation mode setting section that sets an observation mode, a diaphragm control section that selects a diaphragm state based on the observation mode, and an image processing section. In the first observation mode, the diaphragm control section stops down the diaphragm (increases the F-number) so that the resolution is lower than that achieved when fully utilizing the performance of the imaging element. In the second observation mode, the diaphragm control section opens the diaphragm to implement the resolution achieved by fully utilizing the performance of the imaging element.

This makes it possible to set a plurality of observation modes, and select the diaphragm state based on the observation mode. In the first observation mode, a deep depth of field can be implemented in spite of a low resolution by increasing the F-number (i.e., increasing the effects of the diffraction limit). In the second observation mode, an image at a resolution achieved by fully utilizing the performance of the imaging element can be acquired in spite of a shallow depth of field by decreasing the F-number (i.e., suppressing the effects of the diffraction limit).

A control method according to one embodiment of the invention includes setting an observation mode, stopping down the diaphragm (increasing the F-number) so that the resolution is lower than that achieved when fully utilizing the performance of the imaging element when the observation mode is the first observation mode, and opening the diaphragm to implement the resolution achieved by fully utilizing the performance of the imaging element when the observation mode is the second observation mode.

This makes it possible to achieve the above effects by applying the above method to a control method instead of an endoscope system.

The above method may be applied to an imaging apparatus instead of an endoscope system. In this case, the imaging apparatus includes an imaging section, an observation mode setting section that sets an observation mode, and a diaphragm control section that selects a diaphragm state based on the observation mode. The diaphragm control section stops down the diaphragm (increases the F-number) so that the resolution is lower than that achieved when fully utilizing the performance of the imaging element when the observation mode is the first observation mode, and opens the diaphragm to implement the resolution achieved by fully utilizing the performance of the imaging element when the observation mode is the second observation mode.

This makes it possible to achieve the above effects by applying the above method to an imaging apparatus instead of an endoscope system.

A noise reduction process and a contour enhancement process based on the observation mode have also been proposed. The details are described later in connection with a first embodiment. A second embodiment illustrates a method that acquires a normal light image and a special light image, detects a lesion area from the special light image, and enhances the lesion area in the normal light image.

2. First Embodiment

Figure 12:
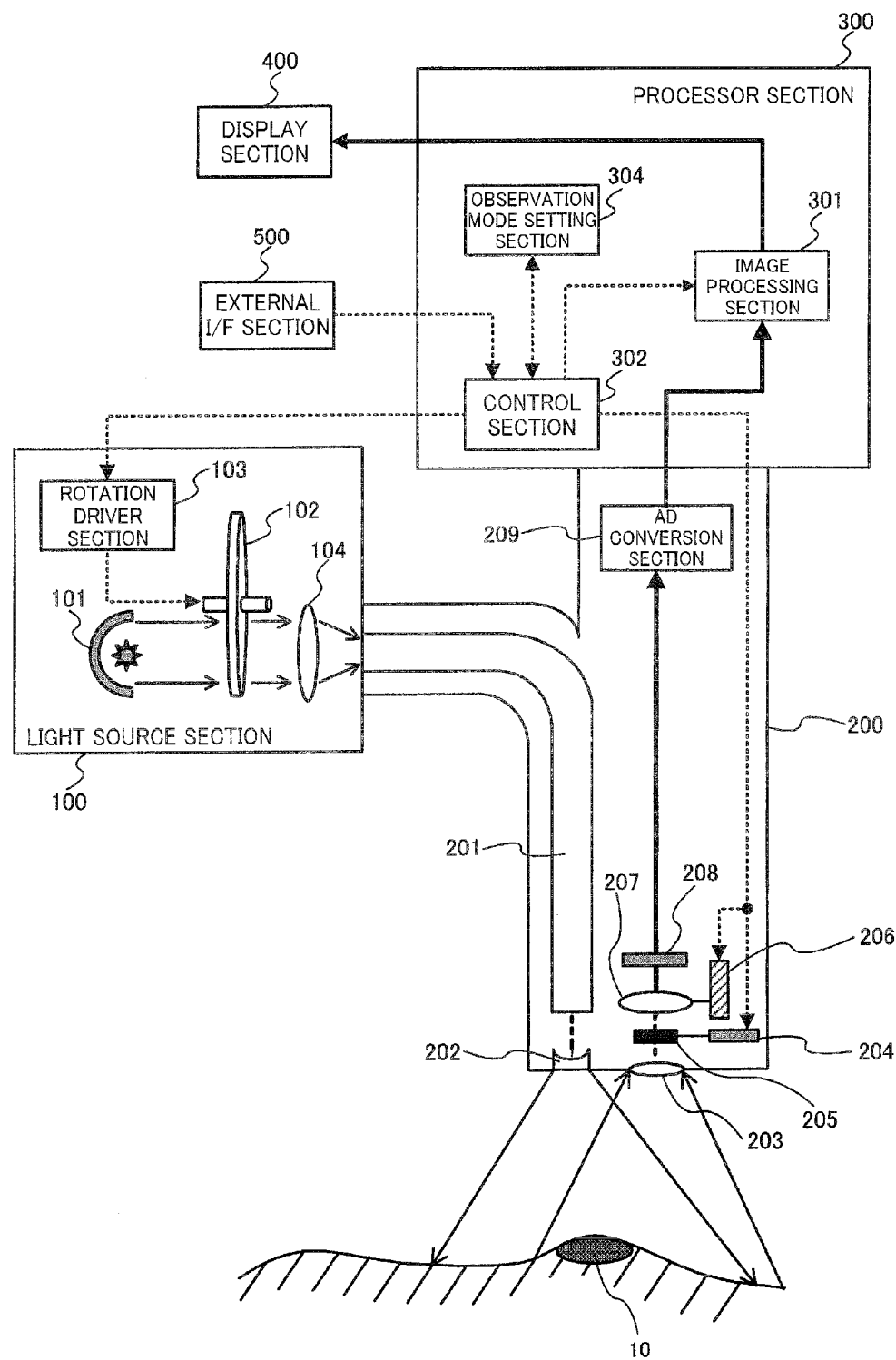
FIG. 12 shows a system configuration example according to one embodiment of the invention.

FIG. 12 is a block diagram showing the entire configuration of an endoscope system (imaging apparatus) according to a first embodiment. The endoscope system according to this embodiment includes a light source section 100, an imaging section 200, a processor section 300, a display section 400, and an external I/F section 500.

The light source section 100 includes a white light source 101, a rotary color filter 102 that has a plurality of spectral transmittances, a rotation driver section 103 that drives the rotary color filter 102, and a condenser lens 104 that focuses light having spectral characteristics that has passed through the rotary color filter 102 on an incident end face of a light guide fiber 201.

Figure 13:
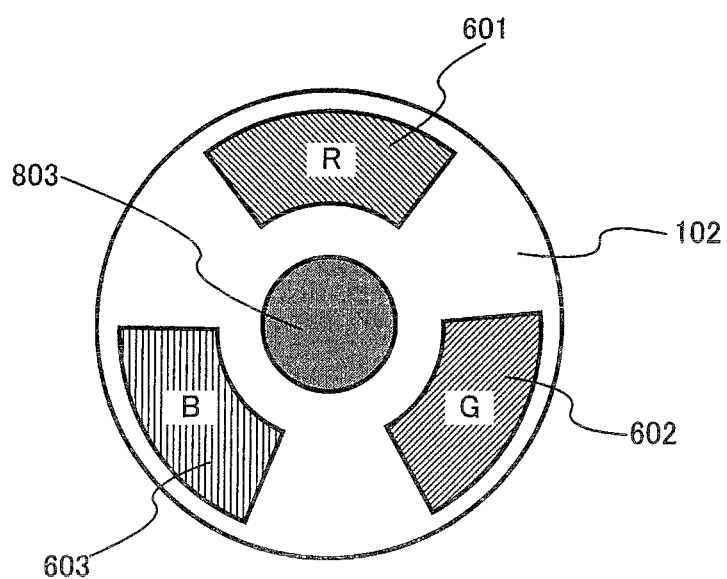
FIG. 13 shows a configuration example of a rotary color filter.
Figure 14:
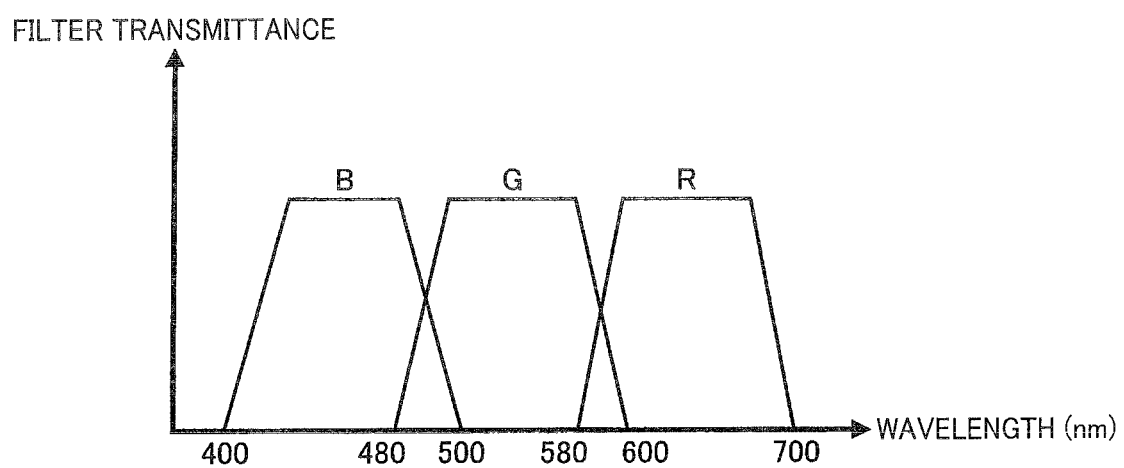
FIG. 14 shows the spectral characteristics of a color filter.

As shown in FIG. 13, the rotary color filter 102 includes a red color filter 601, a green color filter 602, a blue color filter 603, and a rotary motor 803, for example. The red color filter 601, the green color filter 602, and the blue color filter 603 have spectral characteristics shown in FIG. 14.

The rotation driver section 103 rotates the rotary color filter 102 at a given rotational speed in synchronization with the imaging period of an imaging element 208 based on a control signal output from a control section 302 of the processor section 300. For example, when rotating the color filter at 20 revolutions per second, each color filter crosses incident white light every 1/60th of a second, and the imaging element 208 completes acquisition and transfer of image data of reflected light in each color (R, G, or B) every 1/60th of a second. The imaging element 208 is a monochrome imaging element. Specifically, the endoscope system according to this embodiment is configured so that R image data, G image data, and B image data are sequentially acquired (imaged or captured) every 1/60th of a second.

The imaging section 200 is formed to be elongated and flexible (i.e., can be curved) so that the imaging section 200 can be inserted into a body cavity, for example. The imaging section 200 includes the light guide fiber 201 that guides light focused by the light source section 100, an illumination lens 202 that diffuses light that has been guided by the light guide fiber 201, and illuminates an observation target, an objective lens 203 that focuses light reflected by the observation target, a variable diaphragm control section 204, a variable diaphragm 205, a focus control section 206, a focus adjustment lens 207, the imaging element 208 that detects the focused reflected light, and an A/D conversion section 209 that converts a photoelectrically converted analog signal output from the imaging element 208 into a digital signal. The imaging element 208 is a monochrome single imaging element, and may be implemented by a CCD sensor, a CMOS sensor, or the like.

The processor section 300 includes an image processing section 301, the control section 302, and an observation mode setting section 304.

The display section 400 is a display device (e.g., CRT or liquid crystal monitor) that can display a video (moving image).

The external I/F section 500 is an interface that allows the user to perform an input operation or the like on the imaging apparatus. The external I/F section 500 includes a power supply switch (power supply ON/OFF switch), a shutter button (photographing operation start button), a mode (e.g., photographing mode) change button, and the like. The external I/F section 500 outputs the input information to the control section 302.

The relationship between the variable diaphragm control section 204, the variable diaphragm 205, the focus control section 206, and the focus adjustment lens 207 of the imaging section 200 and the control section 302 is described in detail below. The endoscope system according to this embodiment has two observation modes. Specifically, the endoscope system has a distant observation mode (deep depth of field, low resolution) and a close observation mode (shallow depth of field, high resolution).

The control section 302 outputs a control signal to the variable diaphragm control section 204 and the focus control section 206 based on a mode change request that is input by the user using the mode switch button of the external I/F section 500. The variable diaphragm control section 204 controls the variable diaphragm 205 based on the input control signal, and the focus control section 206 controls the focus adjustment lens 207 based on the input control signal.

Figure 15A:
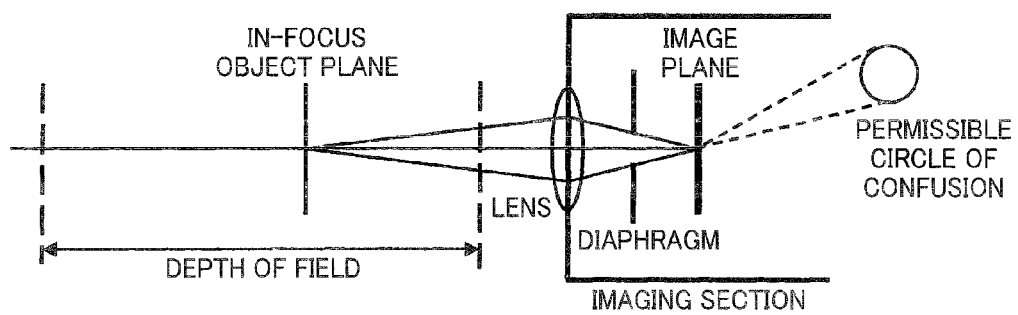
FIG. 15A a view illustrative of the diaphragm and the permissible circle of confusion when selecting a distant observation mode, and FIG. 15B a view illustrative of the diaphragm and the permissible circle of confusion when selecting a close observation mode.
Figure 15B:
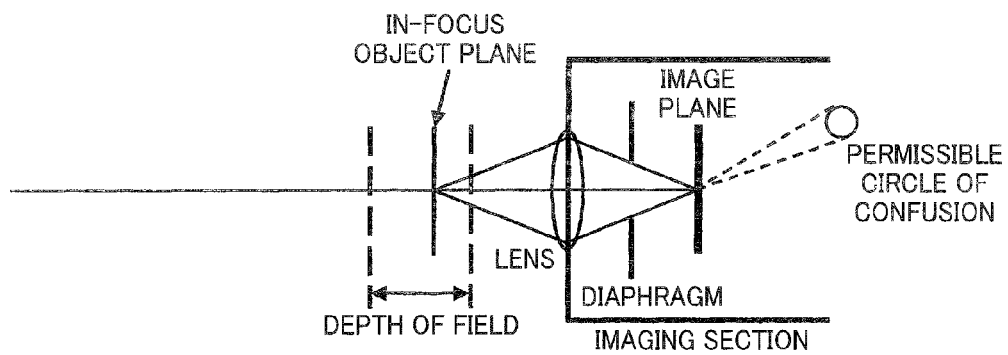

Specifically, when the close observation mode has been selected (see FIG. 15B), the variable diaphragm control section 204 opens the variable diaphragm 205 so that the permissible circle of confusion is set to a state in which the maximum resolution of the imaging element 208 is achieved. The focus control section 206 drives the focus adjustment lens so that a given in-focus object plane is achieved. This limits the depth of field (i.e., a shallow depth of field is obtained), but makes it possible to obtain a high-resolution image at a given in-focus object plane by fully utilizing the performance of the imaging element.

When the distant observation mode has been selected (see FIG. 15A), the variable diaphragm control section 204 stops down the variable diaphragm 205 so that the permissible circle of confusion has a size that achieves a practical resolution and a practical depth of field. The expression "practical resolution" refers to a resolution that is lower than the maximum resolution of the imaging element 208 and is almost equal to the resolution of an imaging element produced by a production process in the preceding generation. For example, the expression "practical resolution" refers to a resolution equivalent to 1.5 to 2 times the pixel pitch of the imaging element 208. The focus control section 206 drives the focus adjustment lens so that an in-focus object plane that implements a practical depth of field is achieved.

The above two modes must be used for the following reason. Specifically, when stopping down the diaphragm of the optical system so that the endoscope has a practical depth of field, the circle of confusion during imaging cannot be reduced with respect to the pixel pitch of the imaging element 208 due to the effects of the diffraction limit.

Specifically, an imaging element that is produced by an advanced semiconductor production process and has a small pixel pitch and an increased number of pixels (i.e., the image height is increased with respect to the pixel pitch) is affected by the diffraction limit to a large extent when stopping down the diaphragm. In particular, a state (deep focus) in which the object is in focus within a practical observation distance is desirable for an endoscope system. The effects of the diffraction limit cannot be disregarded since it is necessary to stop down the diaphragm in order to obtain the desired depth of field.

Figure 16:
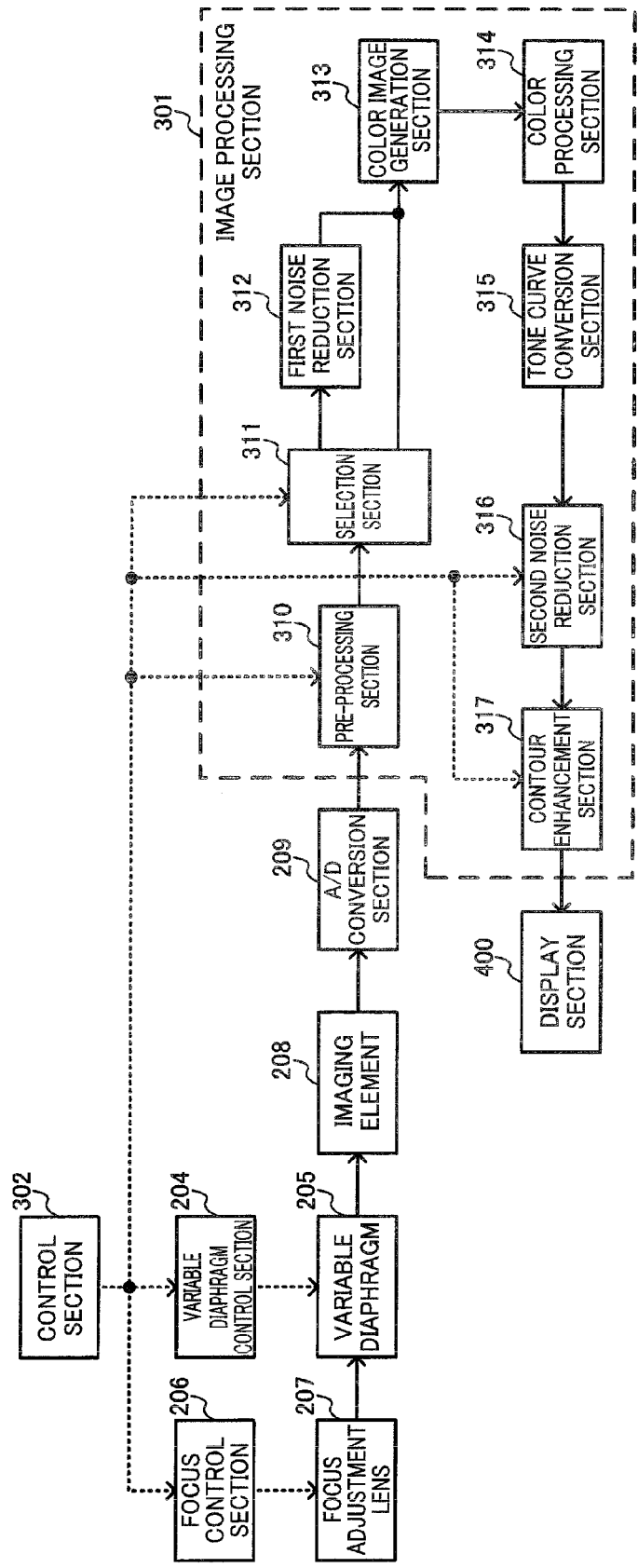
FIG. 16 shows a configuration example of an image processing section.

The details of the image processing section 301 are described below with reference to FIG. 16 (block diagram). The image processing section 301 includes a pre-processing section 310, a selection section 311, a first noise reduction section 312, a color image generation section 313, a color processing section 314, a tone curve conversion section 315, a second noise reduction section 316, and a contour enhancement section 317.

A data flow between each section is described below. The image data output from the A/D conversion section 209 is input to the pre-processing section 310 of the image processing section 301. An OB clamp value, a gain correction value, and a WB coefficient value stored in the control section 302 are also input to the pre-processing section 310. The pre-processing section 310 performs an OB clamp process, a gain correction process, and a WB process on the image data based on the input values, and outputs the resulting image data to the selection section 311.

Figure 17:
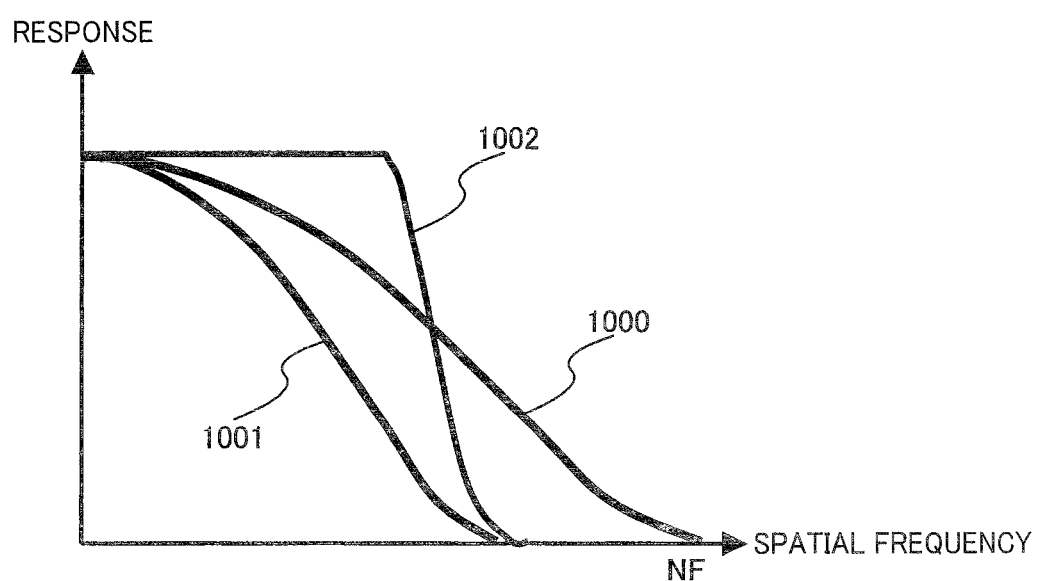
FIG. 17 shows an example of the spatial frequency characteristics of image data in a first observation mode and a second observation mode.

The selection section 311 also receives observation mode information output from the control section 302. The selection section 311 outputs the input image data to the first noise reduction section 312 when the observation mode information indicates the distant observation mode, and outputs the input image data to the color image generation section 313 when the observation mode information indicates the close observation mode. FIG. 17 shows an example of the MTF (spatial frequency characteristics) of the input image data. An MTF 1000 is the MTF in the close observation mode, and an MTF 1001 is the MTF in the distant observation mode. In the distant observation mode, high-frequency components are removed due to the effects of the diffraction limit.

The first noise reduction section 312 subjects the input image data to a low-pass filter having frequency characteristics 1002 shown in FIG. 17 taking account of the fact that the input image data has the MTF 1001. This makes it possible to block only undesired high-frequency noise within a band corresponding to the cut-off band of the low-pass filter.

The image data that is output from the first noise reduction section 312 and has been reduced in noise, or the image data output from the selection section 311, is input to the color image generation section 313.

The color image generation section 313 includes a buffer memory that stores the R image data, the G image data, and the B image data that are input in time series. The color image generation section 313 generates color image data that includes RGB signals per pixel using newly input color signal image data, and outputs the color image data to the color processing section 314.

The color processing section 314 converts the input color image data to have a color space corresponding to the color gamut of the output monitor, and outputs the converted color image data to the tone curve conversion section 315. The color gamut is an sRGB color gamut, for example.

The tone curve conversion section 315 converts the input color image data into color image data (e.g., 8-bit data) that has gamma characteristics that negate the output tone curve characteristics of the display section 400, and outputs the resulting color image data to the second noise reduction section 316.

Figure 18:
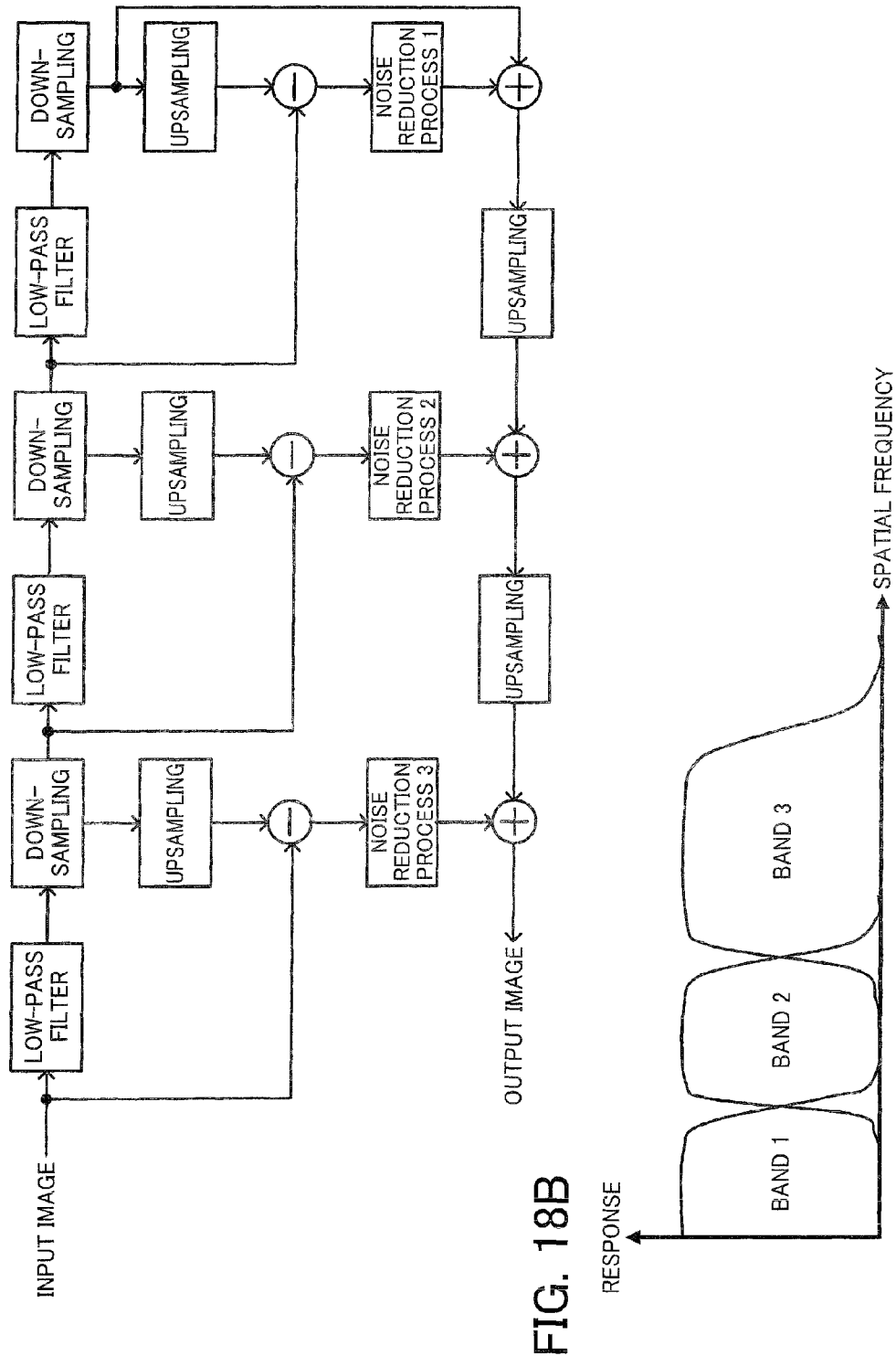
FIG. 18A is a view illustrative of a process using a Laplacian pyramid.
FIG. 18B shows an example in which data is separated into a plurality of frequency bands.

The second noise reduction section 316 generates a Laplacian pyramid multi-resolution image from the input color image data, for example. The second noise reduction section 316 performs a noise reduction process with a given amount of noise reduction on each image that differs in resolution. FIGS. 18A and 18B show the details of the process using the Laplacian pyramid. As shown in FIG. 18A, the difference between the data that is not subjected to the low-pass filter and the data that has been subjected to the low-pass filter is calculated to separate the data into a plurality of spatial frequency bands (see FIG. 18B).

This makes it possible to reduce low-frequency noise (e.g., color noise). The amount of noise reduction from the multi-resolution image may be changed based on the observation mode information input from the control section 302. For example, since high-frequency signal components have been removed in the distant observation mode, it may be determined that a high-frequency image contains a large amount of noise components, and the amount of noise reduction from the high-frequency image may be increased as compared with the close observation mode. In the example shown in FIGS. 18A and 18B, the noise reduction effect is expected to be improved in the distant observation mode by increasing the strength of the noise reduction process (i.e., increasing the amount of noise reduction) on a band 3 as compared with bands 1 and 2. The color image data subjected to the second noise reduction process is output to the contour enhancement section 317.

The contour enhancement section 317 receives the observation mode information output from the control section 302 in addition to the color image data subjected to the second noise reduction process, and outputs the color image data subjected to a contour enhancement process based on the observation mode information to the display section 400.

Figure 19:
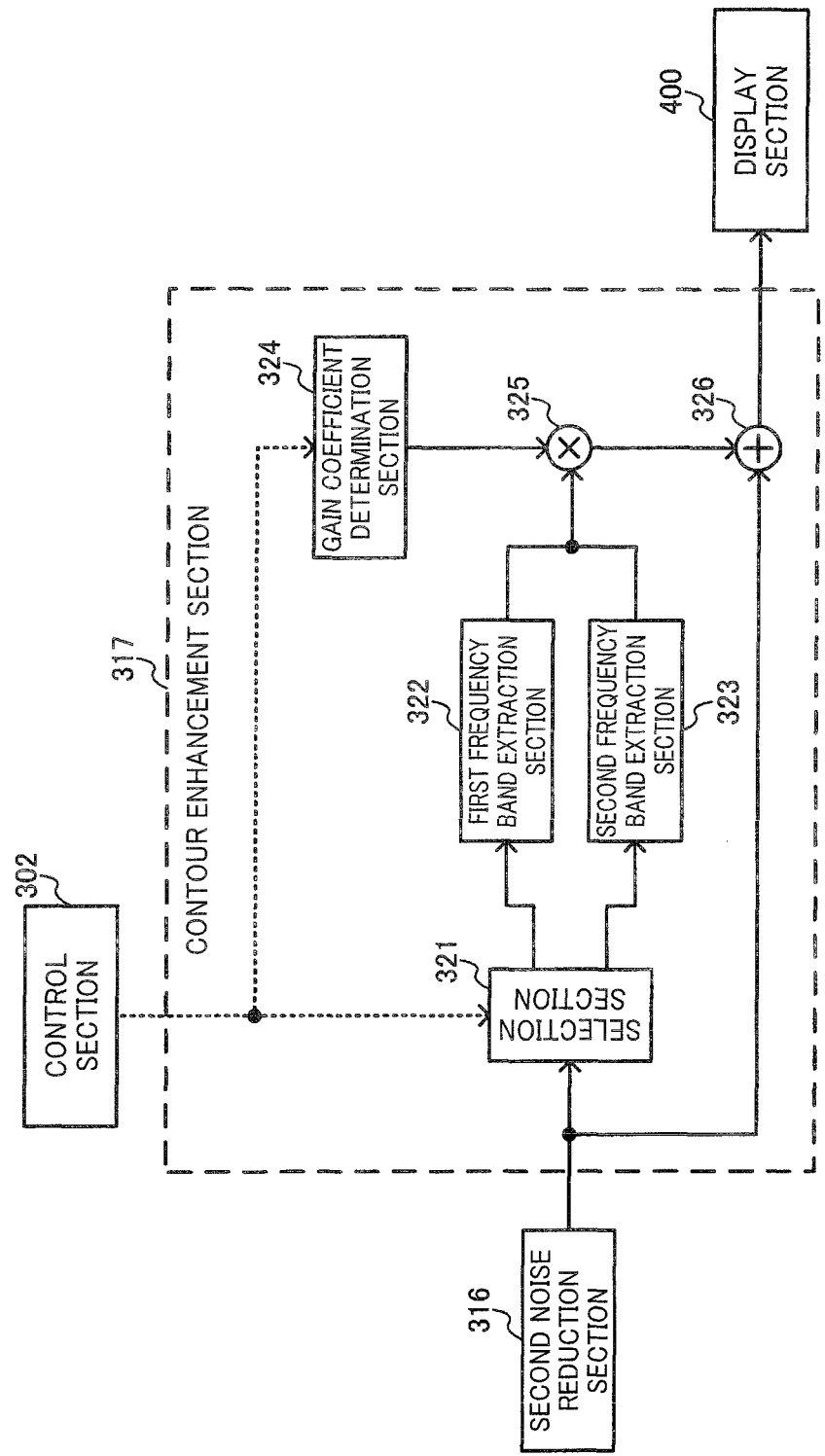
FIG. 19 shows a configuration example of a contour enhancement section.

The details of the contour enhancement section 317 are described below with reference to FIG. 19 (block diagram) and FIG. 20 (enhancement frequency characteristics).

The contour enhancement section 317 includes a selection section 321, a first frequency band extraction section 322, a second frequency band extraction section 323, a gain coefficient determination section 324, a multiplier 325, and an adder 326.

A data flow between each section is described below. The color image data output from the second noise reduction section 316 is input to the selection section 321. The color image data output from the selection section 321 is input to the first frequency band extraction section 322 when the observation mode information output from the control section 302 indicates the distant observation mode, and input to the second frequency band extraction section 323 when the observation mode information output from the control section 302 indicates the close observation mode.

Figure 20:
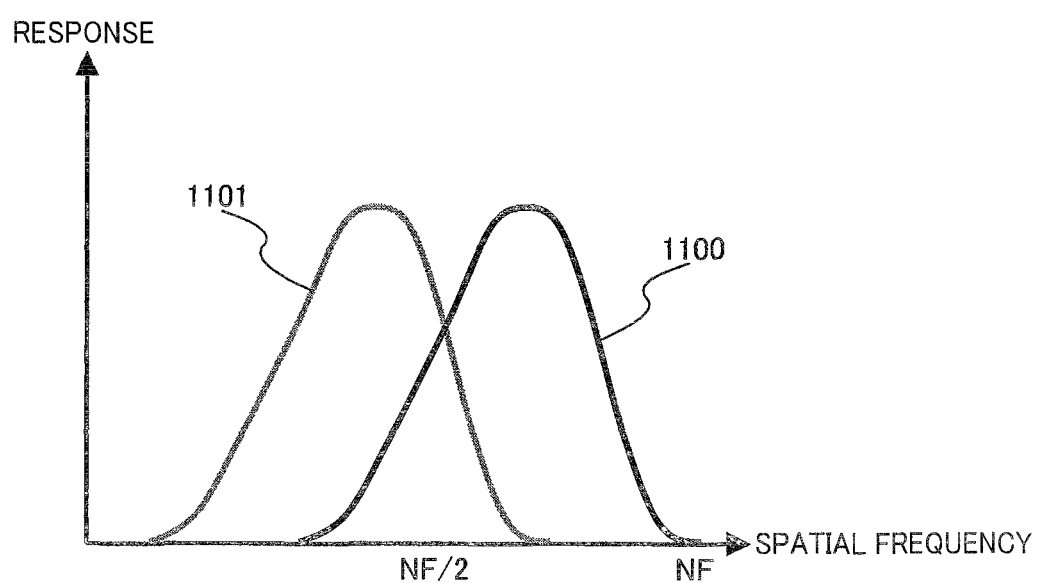
FIG. 20 shows enhancement frequency characteristics in a contour enhancement process.

The first frequency band extraction section 322 includes a band-pass filter corresponding to enhancement frequency characteristics 1101 shown in FIG. 20, and filters the input color image data. A first contour image thus extracted is output to the multiplier 325.

The second frequency band extraction section 323 includes a band-pass filter corresponding to enhancement frequency characteristics 1100 shown in FIG. 20, and filters the input color image data. A second contour image thus extracted is output to the multiplier 325.

In the close observation mode, it suffices to enhance high-frequency components. In the distant observation mode, however, since high-frequency signal components have been removed, the enhancement target contour information is considered to be included in a low frequency band as compared with the close observation mode.

The gain coefficient determination section 324 converts enhancement level information output from the control section 302 into a gain of the contour image having a specific frequency extracted by the first frequency band extraction section 322 or the second frequency band extraction section 323, and outputs the gain to the multiplier 325.

The multiplier 325 multiplies the contour image having a specific frequency extracted by the first frequency band extraction section 322 or the second frequency band extraction section 323 by the gain output from the gain coefficient determination section 324, and outputs the resulting contour image to the adder 326.

The adder 326 adds the contour image to the color image data input to the contour enhancement section 317 to generate a contour-enhanced image, and outputs the contour-enhanced image data to the display section 400.

According to the first embodiment, a high-quality image can be obtained in each observation mode by performing image processing suitable for the frequency characteristics of each observation mode, so that an optimum observation can be implemented depending on the objective.

In particular, even when the original resolution of the imaging element cannot be obtained with respect to a small pixel pitch due to the effects of the diffraction limit based on the diaphragm of the optical system, the object can be observed at the maximum resolution of the imaging element by setting a mode that achieves a deep depth of field and low resolution and a mode that achieves a shallow depth of field and high resolution.

According to the first embodiment, the image processing section 301 reduces high-frequency components in the first observation mode as compared with the second observation mode.

This makes it possible to efficiently reduce noise in the first observation mode. This is because the resolution has decreased (i.e., high-frequency signal components have been removed) in the first observation mode due to the effects of the diffraction limit. Specifically, since it is likely that high-frequency components serve as noise, it is considered that the signal value is affected to only a small extent even if high-frequency components are reduced. Specifically, the image processing section 301 performs the low-pass filter process.

The image processing section 301 increases the amount of noise reduction in the first observation mode as compared with the second observation mode.

This makes it possible to efficiently reduce noise in the first observation mode. This is because high-frequency signal components have been removed in the first observation mode due to the effects of the diffraction limit. Specifically, the image processing section 301 separates the data into a plurality of frequency bands by applying the Laplacian pyramid shown in FIGS. 18A and 18B. In the example shown in FIGS. 18A and 18B, the image processing section 301 increases the amount of noise reduction from the band 3.

The image processing section 301 performs the contour enhancement process that enhances a given high-frequency band in the second observation mode, and performs the contour enhancement process that enhances a low-frequency band lower than given high-frequency band in the first observation mode.

This makes it possible to perform an efficient contour enhancement process depending on the observation mode. This is because high-frequency signal components have been removed in the first observation mode due to the effects of the diffraction limit. Specifically, the image processing section 301 enhances the enhancement frequency characteristics 1100 in the second observation mode, and enhances the enhancement frequency characteristics 1101 in the first observation mode (see FIG. 20).

The first observation mode may be the distant observation mode, and the second observation mode may be the close observation mode.

This makes it possible to determine the application taking account of the characteristics of each mode. In the first observation mode, a deep depth of field is achieved. Therefore, the first observation mode may be used as the distant observation mode of the endoscope system employed when it is desirable that both a close area and a distant area be in focus (e.g., when searching for a lesion area inside a hollow organ). The second observation mode may be used as the close observation mode employed when resolution is given priority over depth of field (e.g., when closely observing a lesion area that has been found).

3. Second Embodiment

Figure 21:
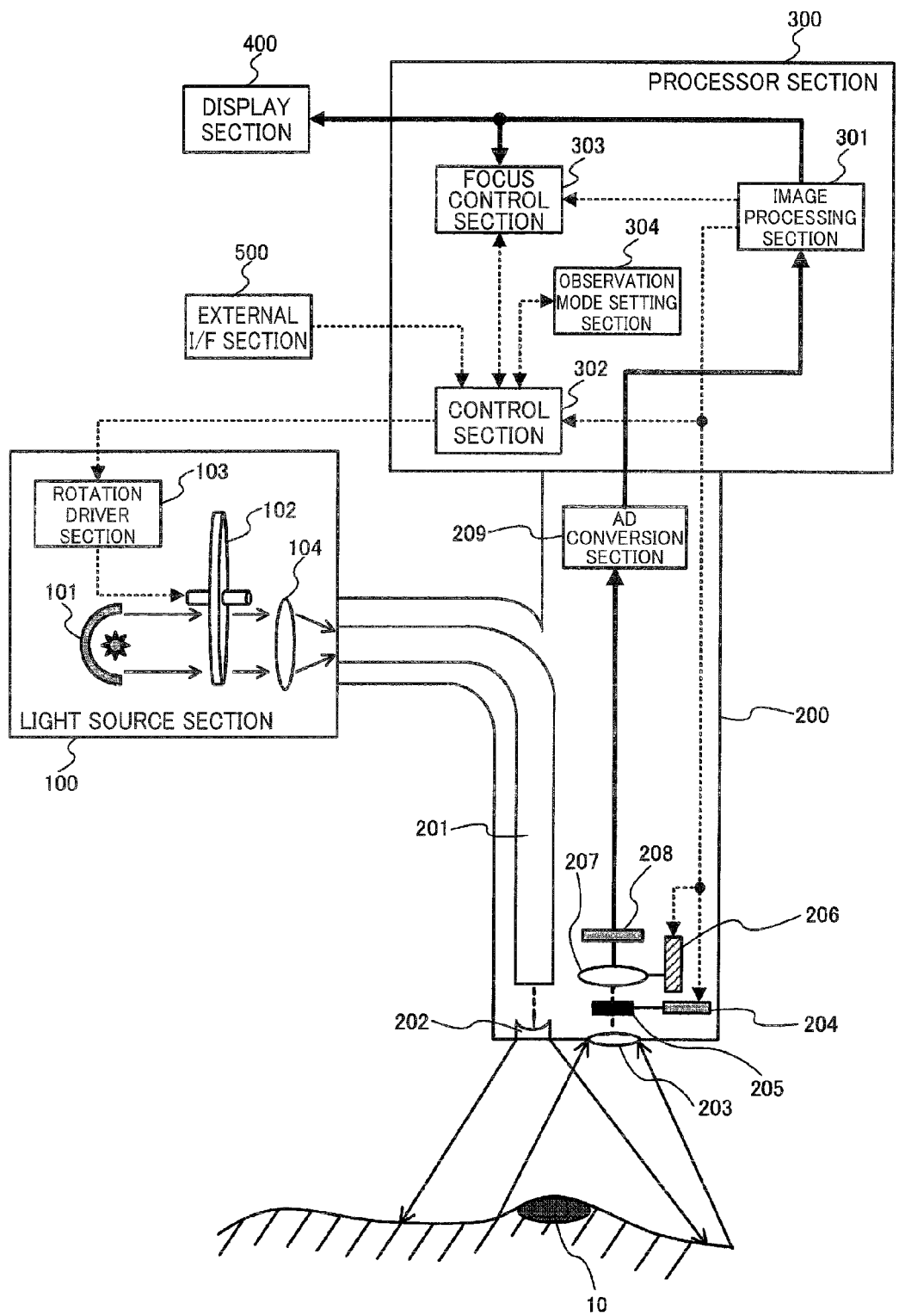
FIG. 21 shows another system configuration example according to one embodiment of the invention.

FIG. 21 is a block diagram showing the entire configuration of an endoscope system (imaging apparatus) according to a second embodiment. The endoscope system according to this embodiment includes a light source section 100, an imaging section 200, a processor section 300, a display section 400, and an external I/F section 500. The basic configuration of the endoscope system according to this embodiment is the same as that of the endoscope system according to the first embodiment. The following description focuses on the differences in configuration between the endoscope system according to this embodiment and the endoscope system according to the first embodiment.

Figure 22:
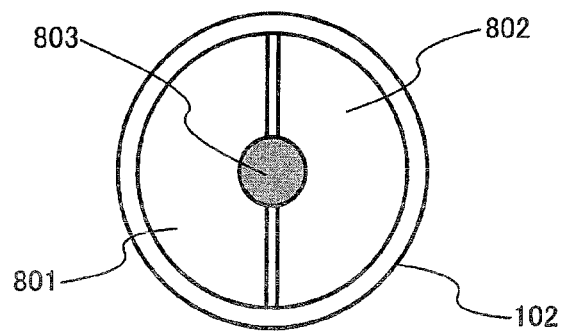
FIG. 22 shows another configuration example of a rotary color filter.
Figure 23:
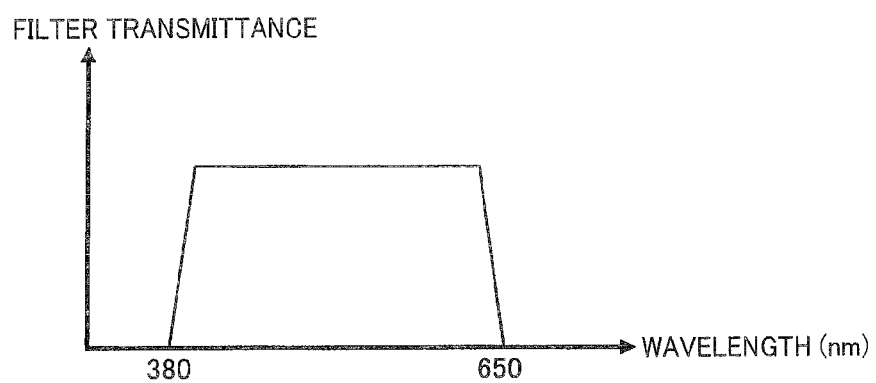
FIG. 23 shows the spectral characteristics of a color filter used for a normal light image.
Figure 24:
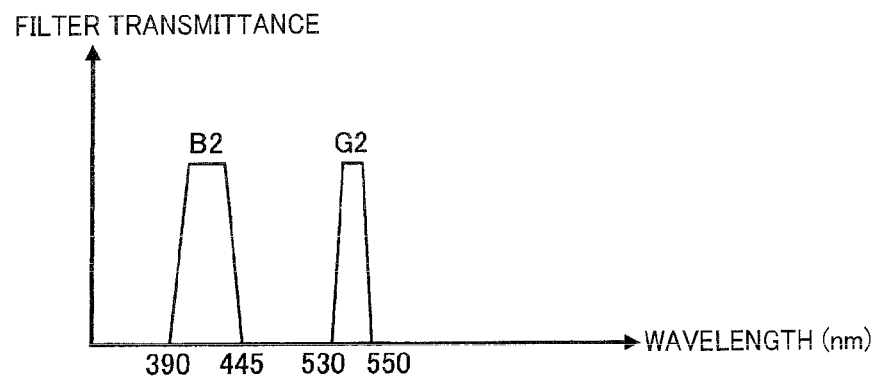
FIG. 24 shows the spectral characteristics of a color filter used for a special light image.

The rotary color filter 102 of the light source section 100 has a configuration shown in FIG. 22. Specifically, the rotary color filter 102 includes a color filter 801 that has a white light spectral transmittance, a color filter 802 that has a narrow-band light (special light) spectral transmittance, and a rotary motor 803. As shown in FIG. 23, the color filter 801 has spectral characteristics that allow light having a wavelength of 380 to 650 nm to pass through, for example. As shown in FIG. 24, the color filter 802 has spectral characteristics that allow light having a wavelength of 390 to 445 nm (B2) or 530 to 550 nm (G2) to pass through, for example.

Figures 25A, 25B:
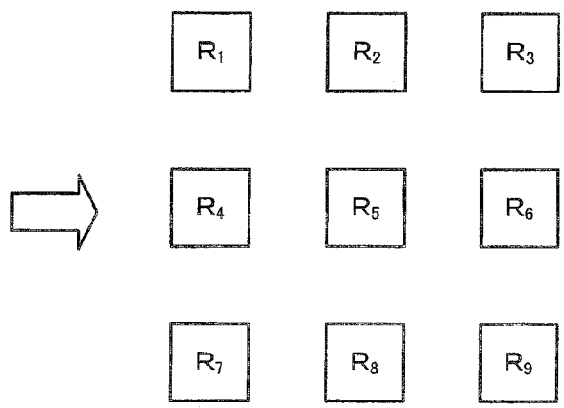
FIG. 25A is a view illustrative of a Bayer array primary color single imaging element.
FIG. 25B is a view illustrative of a signal R image data.

A Bayer array primary color single imaging element shown in FIG. 25A is used as the imaging element 208 of the imaging section 200.

The processor section 300 further includes a focus control section 303. The details of the image processing section 301 differ from those of the first embodiment, and the control process of the control section 302 is changed due to the addition of the focus control section 303 and the change in the rotary color filter 102.

Figure 26:
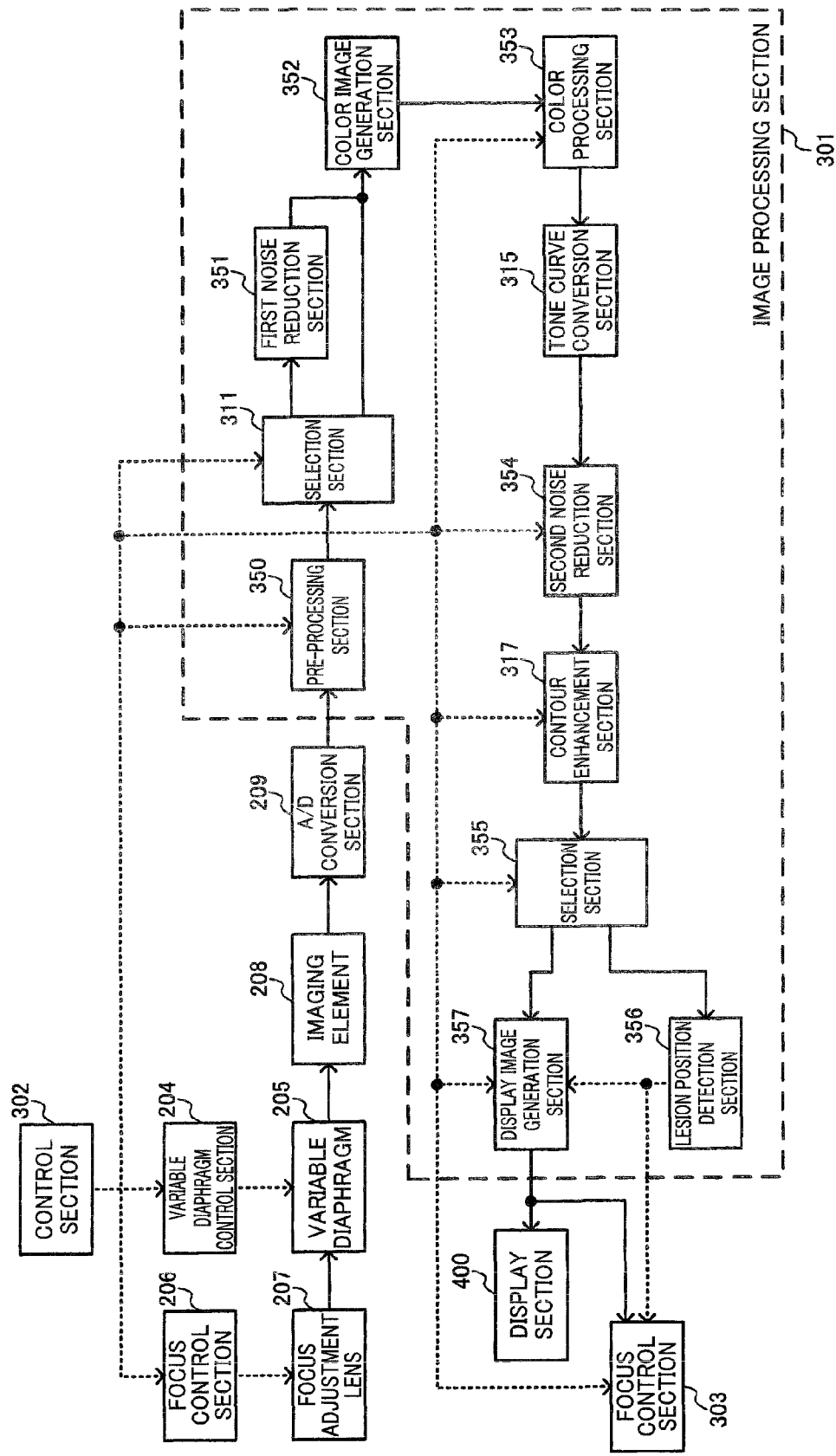
FIG. 26 shows another configuration example of an image processing section.

The details of the image processing section 301 are described below with reference to FIG. 26 (block diagram). The image processing section 301 includes a pre-processing section 350, a selection section 311, a first noise reduction section 351, a color image generation section 352, a color processing section 353, a tone curve conversion section 315, a second noise reduction section 354, a contour enhancement section 317, a selection section 355, a lesion position detection section 356, and a display image generation section 357.

A data flow between each section is described below. The image data output from the A/D conversion section 209 is input to the image processing section 301. An OB clamp value, a gain correction value, and a WB coefficient value corresponding to each color signal stored in the control section 302 are input to the pre-processing section 350. The pre-processing section 350 performs the OB clamp process, the gain correction process, and the WB process on the image data based on the input values, and outputs the resulting image data to the selection section 311.

The selection section 311 also receives the observation mode information output from the control section 302. The selection section 311 outputs the input image data to the first noise reduction section 351 when the observation mode information indicates the distant observation mode, and outputs the input image data to the color image generation section 352 when the observation mode information indicates the close observation mode. FIG. 17 shows an example of the MTF (spatial frequency characteristics) of the input image data. The MTF 1000 is the MTF in the close observation mode, and the MTF 1001 is the MTF in the distant observation mode. In the distant observation mode, high-frequency components are removed due to the effects of the diffraction limit.

The first noise reduction section 351 subjects the input image data including each color signal (signal R) shown in FIG. 25B to a low-pass filter having the frequency characteristics 1002 shown in FIG. 17 taking account of the fact that the input image data has the MTF 1001. This makes it possible to block only high-frequency noise within a band corresponding to the cut-off band of the low-pass filter.

The image data that is output from the first noise reduction section 351 and has been reduced in noise, or the image data output from the selection section 311, is input to the color image generation section 352.

The color image generation section 352 also receives illumination light type (white light or special light) information output from the control section 302. The color image generation section 352 generates two missing signals of each pixel by an interpolation process that differs depending on the illumination light type information based on the Bayer array to generate color image data that includes RGB signals per pixel, and outputs the color image data to the color processing section 353.

The color processing section 353 also receives the illumination light type (white light or special light) information output from the control section 302. The color processing section 353 converts the input color image data to have a color space corresponding to the color gamut of the output monitor when the illumination light is white light, and converts the input color image data to have a given pseudo-color when the illumination light is special light. The color processing section 353 then outputs the converted color image data to the tone curve conversion section 315. The color gamut is an sRGB (standard RGB) color gamut, for example.

The tone curve conversion section 315 converts the input color image data into color image data (e.g., 8-bit data) that has gamma characteristics that negate the output tone curve characteristics of the display section 400, and outputs the resulting color image data to the second noise reduction section 354.

The second noise reduction section 354 also receives the illumination light type (white light or special light) information and imaging mode information output from the control section 302. The second noise reduction section 354 generates a Laplacian pyramid multi-resolution image from the input color image data, for example. The second noise reduction section 354 performs a noise reduction process with a given amount of noise reduction on each image that differs in resolution based on the illumination light type information and the imaging mode information. This makes it possible to reduce low-frequency noise (e.g., color noise), and implement an effective noise reduction process that overcomes an increase in noise due to an insufficient quantity of light when using special light. The color image data subjected to the second noise reduction process is output to the edge enhancement section 317.

The contour enhancement section 317 receives the observation mode information output from the control section 302 in addition to the color image data that has been reduced in noise. The contour enhancement section 317 performs the contour enhancement process based on the observation mode information in the same manner as in the first embodiment to generate a contour-enhanced color image data, and outputs the contour-enhanced color image data to the selection section 355. The contour enhancement section 317 may also receive the illumination light type information output from the control section 302, and may change the amount of enhancement depending on the illumination light.

The selection section 355 also receives the illumination light type information output from the control section 302. The selection section 355 outputs the color image data obtained using special light to the lesion position detection section 356, and outputs the color image data obtained using white light to the display image generation section 357. A color image that has been obtained by applying special light and includes an object image including information within a specific wavelength band is hereinafter referred to as "special light image". A color image that has been obtained by applying white light and includes an object image including information within a white light wavelength band is hereinafter referred to as "white light image".

The lesion position detection section 356 extracts an area having a given hue from the input special light image, groups adjacent areas, and determines whether or not the area obtained by grouping is equal to or larger than a given threshold value. When the lesion position detection section 356 has determined that the area obtained by grouping is equal to or larger than the given threshold value, the lesion position detection section 356 sets a rectangular or circular area that encloses the area obtained by grouping as a lesion area, and outputs the lesion area to the display image generation section 357 and the focus control section 303 as a lesion position. When a plurality of lesion positions have been detected, a lesion having the maximum area is selected, for example. When a plurality of lesion positions still remain, a lesion positioned closer to the center of the screen is selected.

The display image generation section 357 generates a display image described later based on the lesion area, the white light image, and display mode information output from the control section 302, and outputs the display image to the display section 400 and the focus control section 303. The focus control section 303 functions only when the observation mode information output from the control section 302 indicates the close observation mode, or when the lesion position has been output from the lesion position detection section 356.

Figure 27:
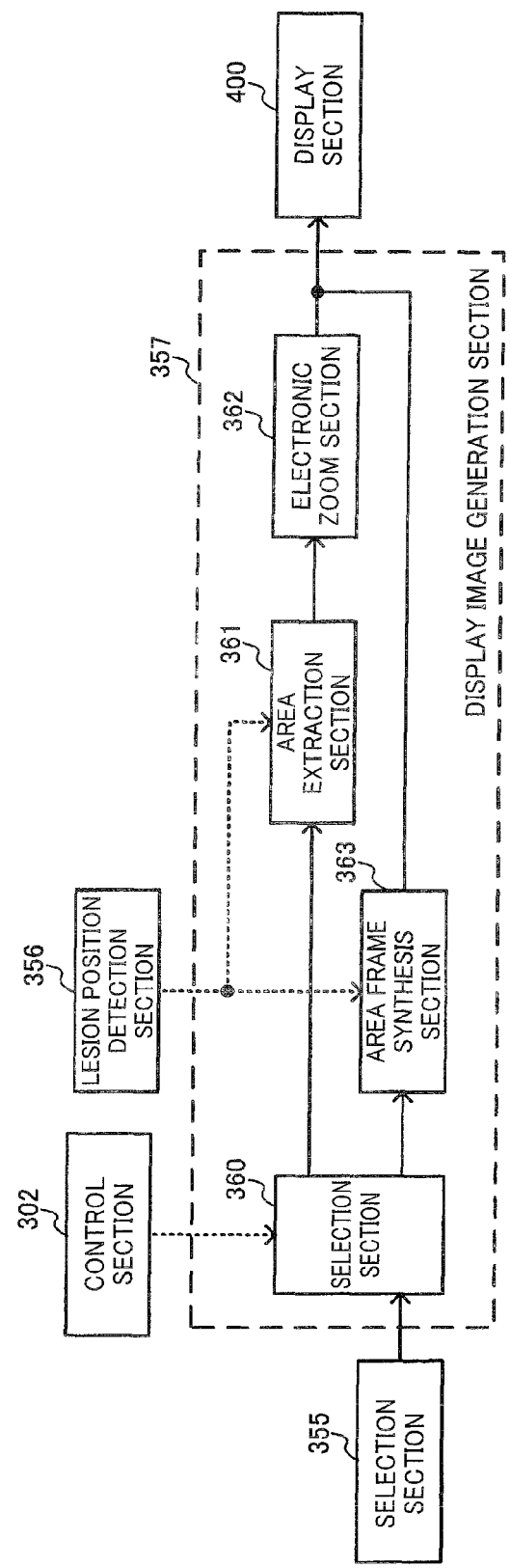
FIG. 27 shows a configuration example of a display image generation section.

The details of the display image generation section 357 are described below with reference to FIG. 27.

The display image generation section 357 includes a selection section 360, an area extraction section 361, an electronic zoom section 362, and an area frame synthesis section 363.

A data flow between each section is described below. The white light image output from the selection section 355 is input to the selection section 360, and then input to the area extraction section 361 when the display mode information output from the control section 302 indicates a lesion area zoom display mode, and input to the area frame synthesis section 363 when the display mode information output from the control section 302 indicates a lesion area frame display mode.

The area extraction section 361 extracts a given area including the lesion position (rectangular or circular area) output from the lesion position detection section 356 from the white light image, and outputs the given area to the electronic zoom section 362. The electronic zoom section 362 performs an electronic zoom process so that the extracted given area has the display screen size of the display section 400, and outputs the given area to the display section 400 and the focus control section 303.

The area frame synthesis section 363 superimposes a rectangular or circular frame that indicates the lesion position (rectangular or circular area) output from the lesion position detection section 356 at the corresponding position of the white light image, and outputs the resulting image to the display section 400 and the focus control section 303.

The display mode is selected by the user using the display mode switch of the external I/F section 500. When the lesion area zoom display mode has been selected, the control section 302 causes the variable diaphragm control section 204 to open the variable diaphragm 205. Specifically, since a high resolution is obtained in the lesion area zoom display mode (i.e., close observation mode) in spite of a shallow depth of field, an image having a sufficient resolution can be displayed even if the electronic zoom process is performed. In this case, it is desirable to utilize an autofocus function described below. Note that practical usability can be obtained in the close observation mode even when using a fixed focus.

Figure 28:
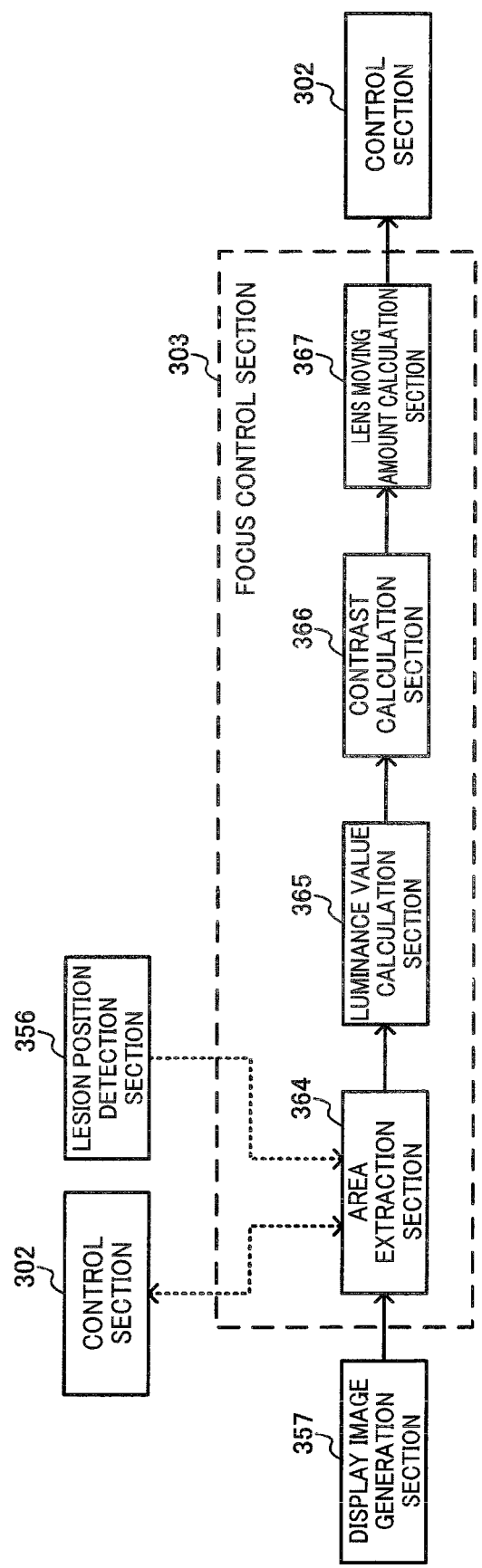
FIG. 28 shows a configuration example of a focus control section.

The details of the focus control section 303 are described below with reference to FIG. 28.

The focus control section 303 includes an area extraction section 364, a luminance value calculation section 365, a contrast calculation section 366, and a lens moving amount calculation section 367.

A data flow between each section is described below. The white light image output from the display image generation section 357 is input to the area extraction section 364, and an area corresponding to the display mode information output from the control section 302 and the lesion position output from the lesion position detection section 356 is extracted from the white light image. When the lesion position detection section 356 has detected the lesion area, and output the lesion position, the area extraction section 364 outputs switch information to the control section 302 so that the control section 302 switches the observation mode information. For example, when an automatic observation mode switch (not shown) included in the external I/F section 500 has been set to ON, the control section 302 switches the observation mode information based on the switch information. For example, the control section 302 switches the observation mode information to the close observation mode when the lesion position detection section 356 has detected a lesion, and switches the observation mode information to the distant observation mode when the lesion position detection section 356 does not detect a lesion. When the automatic observation mode switch has been set to OFF, the focus control section 303 does not operate as long as the user does not set the observation mode to the close observation mode.

When the lesion position detection section 356 has output a lesion position, the luminance value calculation section 365 converts the lesion area extracted by the area extraction section 364 from the color image data into luminance values, and outputs the luminance values to the contrast calculation section 366.

The contrast calculation section 366 calculates the maximum luminance value and the minimum luminance value within the lesion area to obtain a contrast value. The contrast values of a plurality of frames are stored in a memory (not shown) included in the contrast calculation section 366 as time series data. At least three contrast values stored in the memory are output to the lens moving amount calculation section 367.

The adjustment position of the focus adjustment lens 207 is stored in a memory (not shown) included in the lens moving amount calculation section 367. The lens moving amount calculation section 367 calculates a lens adjustment position (i.e., position corresponding to an in-focus object plane) from the adjustment position corresponding to at least three input contrast values, and outputs the lens adjustment position to the control section 302. The control section 302 outputs the lens adjustment position to the focus control section 206, and the focus control section 206 moves the focus adjustment lens 207 to implement autofocus on the lesion position.

According to the second embodiment, the observation mode can be automatically switched between the distant observation mode and the close observation mode based on the lesion detection result, and the lesion position can be automatically brought into focus when the close observation mode has been selected. Therefore, the user need not perform a troublesome mode switch operation, and can concentrate on a lesion diagnosis. Since the observation mode is automatically switched to the high-resolution close observation mode when electronically zooming in the area including the detected lesion position, the user can make a lesion diagnosis using a high-quality image having a sufficient resolution in the same manner as in the distant observation mode.

According to the second embodiment, the lesion position detection section detects a lesion position from the acquired image. When the lesion position detection section has detected a lesion position, the observation mode setting section 304 sets the observation mode to the second observation mode.

This makes it possible to set the observation mode to the second observation mode (shallow depth of field, high resolution) when a lesion position has been detected. Specifically, when a lesion position has been detected, the user is likely to observe a narrow range around the lesion area instead of observing a wide range.

The image processing section 301 acquires a first image that includes an object image including information within a specific wavelength band that is narrower than that of white light, and the lesion position detection section 356 detects a lesion position based on the first image.

This makes it possible to detect a lesion area by narrow-band observation. For example, when using an NBI mode, the visibility of a specific lesion can be improved by narrow-band observation (e.g., a specific lesion (e.g., epidermoid cancer) is displayed as a brown area) as compared with white light observation. Therefore, a lesion position can be effectively detected by utilizing narrow-band light.

The focus control section 303 may control the in-focus object plane when the observation mode is the second observation mode. The focus control section 303 may bring a predetermined fixed plane or a lesion area into focus.

This makes it possible to control the in-focus object plane, so that the object can be appropriately brought into focus even in the second observation mode that achieves a shallow depth of field. The focus control section 303 may bring a predetermined average in-focus object plane into focus in the second observation mode. When the lesion position detection section 356 has detected a lesion area, the focus control section 303 may bring the lesion position into focus since the user is likely to observe an area around the lesion area.

The image processing section 301 may acquire a second image that includes an object image including information within a white light wavelength band in addition to the first image, and the object may be brought into focus based on the contrast of a given area of the second image. Note that the second image includes the lesion position detected from the first image.

This makes it possible to acquire the first image (i.e., special light image) and the second image (i.e., normal light image), and focus on the object by a contrast method using the second image.

The electronic zoom section 362 may zoom in an area including the lesion position that has been brought into focus by the focus control section 303 at a given magnification.

This makes it possible to zoom in the lesion position, so that the lesion position can be more closely observed. The resolution decreases due to the electronic zoom process. However, since the high-resolution second observation mode is used when the lesion position has been detected, a practical resolution can be obtained.

The image processing section 301 acquires the first image (i.e., special light image) and the second image (i.e., normal light image). The first image and the second image are in vivo images. The specific wavelength band included in the in vivo image is the wavelength band of a wavelength absorbed by hemoglobin in blood. The wavelength absorbed by hemoglobin is 390 to 445 nm (i.e., component B2 of narrow-band light) or 530 to 550 nm (i.e., component G2 of narrow-band light), for example.

This makes it possible to implement narrow-band observation referred to as narrow-band imaging (NBI), so that the structure of a surface area of a tissue and a vessel located in a deep area can be observed. A lesion area (e.g., epidermoid cancer) that cannot be easily observed using normal light can be displayed as a brown area or the like in light by inputting the resulting signal to a given channel (G2→R, B2→G and B), so that the lesion area can be reliably detected. A wavelength of 390 to 445 non or 530 to 550 nm is selected from the viewpoint of absorption by hemoglobin and the ability to reach a surface area or a deep area of a tissue. Note that the wavelength band is not limited thereto. For example, the lower limit of the wavelength band may decrease by about 0 to 10%, and the upper limit of the wavelength band may increase by about 0 to 10% depending on a variation factor (e.g., experimental results for absorption by hemoglobin and the ability to reach a surface area or a deep area of a tissue).

The specific wavelength band included in the in vivo image may be the wavelength band of fluorescence emitted from a fluorescent substance. For example, the specific wavelength band may be 490 to 625 nm.

This enables autofluorescence imaging (AFI). Intrinsic fluorescence (490 to 625 nm) from a fluorescent substance (e.g., collagen) can be observed by applying excitation light (390 to 470 nm). In this case, the lesion area can be highlighted in a color differing from that of a normal mucous membrane, so that the lesion area can be reliably detected, for example. A wavelength band of 490 to 625 nm is the wavelength band of fluorescence emitted from a fluorescent substance (e.g., collagen) when excitation light is applied. A wavelength band of 390 to 470 nm is the wavelength band of excitation light that causes fluorescence to occur.

Note that the wavelength band is not limited thereto. For example, the lower limit of the wavelength band may decrease by about 0 to 10%, and the upper limit of the wavelength band may increase by about 0 to 10% depending on a variation factor (e.g., experimental results for the wavelength band of fluorescence emitted from a fluorescent substance). A pseudo-color image may be generated by applying light within a wavelength band of 540 to 560 nm that is absorbed by hemoglobin.

The specific wavelength band included in the in vivo image may be an infrared wavelength band. For example, the specific wavelength band may be 790 to 820 nm or 905 to 970 nm.

This enables infrared imaging (IRI). Information about the vessel or the blood flow in a deep area of the mucous membrane that cannot be easily observed visually can be highlighted by intravenously injecting indocyanine green (ICG) (infrared marker) that easily absorbs infrared light, and applying infrared light within the above wavelength band, so that the depth of cancer invasion or the therapeutic strategy can be determined, for example. An infrared marker exhibits maximum absorption in a wavelength band of 790 to 820 nm, and exhibits minimum absorption in a wavelength band of 905 to 970 nm. Note that the wavelength band is not limited thereto. For example, the lower limit of the wavelength band may decrease by about 0 to 10%, and the upper limit of the wavelength band may increase by about 0 to 10% depending on a variation factor (e.g., experimental results for absorption by the infrared marker).

An example in which the image processing section 301 acquires both the first image (special light image) and the second image (normal light image) has been described above. Note that another configuration may be employed. For example, the special light image may be used to detect a lesion position and displayed on the display section 400, or the normal light image may be used to detect a lesion position and displayed on the display section 400.

The first and second embodiments according to the invention and the modifications thereof have been described above. Note that the invention is not limited to the first and second embodiments and the modifications thereof. Various modifications and variations may be made without departing from the scope of the invention. A plurality of elements of each of the first and second embodiments and the modifications thereof may be appropriately combined. For example, some elements may be omitted from the elements of the first and second embodiments and the modifications thereof. The elements described in connection with the above embodiments and the modifications thereof may be appropriately combined. Specifically, various modifications and applications are possible without materially departing from the novel teachings and advantages of the invention.

Any term or expression (e.g., increasing the F-number) cited with a different term or expression (e.g., stopping down the diaphragm) having a broader meaning or the same meaning at least once in the specification and the drawings may be replaced by the different term in any place in the specification and the drawings.

What is claimed is:
1. An endoscope system comprising:
   an imaging section comprising:
      an imaging optical system; and
      an imaging element;
   an observation mode setting section configured to set an object observation mode as a distant observation mode or a close observation mode;
   a diaphragm control section configured to select a diaphragm state of the imaging optical system based on the observation mode set by the observation mode setting section; and
   an image processing section configured to process an image acquired by the imaging section, wherein the diaphragm control section is configured to select a first diaphragm state when the observation mode is the distant observation mode, the first diaphragm state being a state in which a resolution determined by a diffraction limit based on a diaphragm of the imaging optical system is lower than a resolution determined by the imaging element, wherein the diaphragm control section is configured to select a second diaphragm state when the observation mode is the close observation mode, the second diaphragm state being a state in which the resolution determined by the diffraction limit based on the diaphragm of the imaging optical system is equal to or higher than the resolution determined by the imaging element, and wherein the image processing section is configured to reduce high-frequency components in the image acquired by the imaging section when the observation mode is the distant observation mode as compared with a case where the observation mode is the close observation mode.

2. An endoscope system comprising:

an imaging section comprising:
an imaging optical system; and
an imaging element;

an observation mode setting section configured to set an object observation mode as a distant observation mode or a close observation mode;

a diaphragm control section configured to select a diaphragm state of the imaging optical system based on the observation mode set by the observation mode setting section; and an image processing section configured to process an image acquired by the imaging section, wherein the diaphragm control section is configured to select a first diaphragm state when the observation mode is the distant observation mode, the first diaphragm state being a state in which a resolution determined by a diffraction limit based on a diaphragm of the imaging optical system is lower than a resolution determined by the imaging element, wherein the diaphragm control section is configured to select a second diaphragm state when the observation mode is the close observation mode, the second diaphragm state being a state in which the resolution determined by the diffraction limit based on the diaphragm of the imaging optical system is equal to or higher than the resolution determined by the imaging element, and wherein the image processing section is configured to increase an amount of noise reduction in the image acquired by the imaging section when the observation mode is the distant observation mode as compared with a case where the observation mode is the close observation mode.

3. The endoscope system as defined in claim 1, wherein the image processing section is configured to perform a contour enhancement process that enhances a given high-frequency band when the observation mode is the close observation mode, and wherein the image processing section is configured to perform a contour enhancement process that enhances a frequency band lower than the given high-frequency band when the observation mode is the distant observation mode.

4. The endoscope system as defined in claim 1, further comprising:

a lesion position detection section configured to detect a lesion position from the image acquired by the imaging section, wherein the observation mode setting section is configured to set the observation mode to the close observation mode when the lesion position detection section has detected the lesion position.

5. The endoscope system as defined in claim 4, wherein the image processing section is configured to acquire a first image that includes an object image including information within a specific wavelength band that is narrower than a wavelength band of white light, and wherein the lesion position detection section is configured to detect the lesion position based on the first image.

6. The endoscope system as defined in claim 4, further comprising:

a focus control section configured to bring a given plane into focus, wherein the focus control section is configured to control an in-focus object plane when the observation mode is the close observation mode.

7. The endoscope system as defined in claim 6, wherein the focus control section is configured to bring a predetermined fixed plane into focus.

8. The endoscope system as defined in claim 6, wherein the focus control section is configured to bring the lesion position into focus.

9. The endoscope system as defined in claim 4, further comprising:

a focus control section configured to bring a given plane into focus, wherein the image processing section is configured to acquire a first image that includes an object image including information within a specific wavelength band that is narrower than a wavelength band of white light, and a second image that includes an object image including information within a wavelength band of white light, wherein the second image includes the lesion position detected from the first image, and wherein the focus control section is configured to bring the given plane into focus based on a contrast of a given area of the second image.

10. The endoscope system as defined in claim 9, further comprising:

an electronic zoom section configured to zoom in on an acquired image, wherein the electronic zoom section is configured to zoom in on an area of the second image including the lesion position that has been brought into focus by the focus control section at a given magnification.

11. The endoscope system as defined in claim 1, wherein the image processing section is configured to acquire a first image that includes an object image including information within a specific wavelength band that is narrower than a wavelength band of white light, and a second image that includes an object image including information within a wavelength band of white light.

12. The endoscope system as defined in claim 11, wherein the first image and the second image are in vivo images, and wherein the specific wavelength band included in the in vivo image is a wavelength band absorbed by hemoglobin in blood.

13. The endoscope system as defined in claim 12, wherein the specific wavelength band is 390 to 445 nm or 530 to 550 nm.

14. The endoscope system as defined in claim 11,
wherein the first image and the second image are in vivo images, and
wherein the specific wavelength band included in the in vivo image is a wavelength band of fluorescence emitted from a fluorescent substance.

15. The endoscope system as defined in claim 14, wherein the specific wavelength band is 490 to 625 nm.

16. The endoscope system as defined in claim 11,
wherein the first image and the second image are in vivo images, and
wherein the specific wavelength band included in the in vivo image is a wavelength band of infrared light.

17. The endoscope system as defined in claim 16, wherein the specific wavelength band is 790 to 820 nm or 905 to 970 nm.

18. A control method comprising:
setting an object observation mode as a distant observation mode or a close observation mode;
selecting a first diaphragm state as a diaphragm state of an imaging optical system when the observation mode is the distant observation mode, the first diaphragm state being a state in which a resolution determined by a diffraction limit based on a diaphragm of the imaging optical system is lower than a resolution determined by an imaging element;
selecting a second diaphragm state as the diaphragm state when the observation mode is the close observation mode, the second diaphragm state being a state in which the resolution determined by the diffraction limit based on the diaphragm of the imaging optical system is equal to or higher than the resolution determined by the imaging element; and
reducing high-frequency components in an image acquired by the imaging element when the observation mode is the distant observation mode as compared with a case where the observation mode is the close observation mode.

19. An imaging apparatus comprising:
an imaging section comprising:
an imaging optical system; and
an imaging element;
an observation mode setting section configured to set an object observation mode as a distant observation mode or a close observation mode;
a diaphragm control section configured to select a diaphragm value of the imaging optical system based on the observation mode set by the observation mode setting section; and
an image processing section configured to process an image acquired by the imaging section,
wherein the diaphragm control section is configured to select a first diaphragm state as the diaphragm value when the observation mode is the distant observation mode, the first diaphragm state being a state in which a resolution determined by a diffraction limit based on a diaphragm of the imaging optical system is lower than a resolution determined by the imaging element,
wherein the diaphragm control section is configured to select a second diaphragm state as the diaphragm value when the observation mode is the close observation mode, the second diaphragm state being a state in which the resolution determined by the diffraction limit based on the diaphragm of the imaging optical system is equal to or higher than the resolution determined by the imaging element, and
wherein the image processing section is configured to reduce high-frequency components in the image acquired by the imaging section when the observation mode is the distant observation mode as compared with a case where the observation mode is the close observation mode.

\* \* \* \* \*